United States Patent
Sasaki

(10) Patent No.: US 11,320,507 B2
(45) Date of Patent: May 3, 2022

(54) NUCLEAR MAGNETIC RESONANCE APPARATUS, MAGNETIC RESONANCE IMAGING APPARATUS, NUCLEAR MAGNETIC RESONANCE METHOD, MAGNETIC RESONANCE IMAGING METHOD, METHOD FOR DETERMINING MEASUREMENT CONDITIONS, AND PROGRAM

(71) Applicant: NIIGATA UNIVERSITY, Niigata (JP)

(72) Inventor: Susumu Sasaki, Niigata (JP)

(73) Assignee: NIIGATA UNIVERSITY, Niigata (JP)

( * ) Notice: Subject to any disclaimer, the term of this patent is extended or adjusted under 35 U.S.C. 154(b) by 25 days.

(21) Appl. No.: 16/976,707

(22) PCT Filed: Mar. 1, 2019

(86) PCT No.: PCT/JP2019/008240
§ 371 (c)(1),
(2) Date: Aug. 28, 2020

(87) PCT Pub. No.: WO2019/168188
PCT Pub. Date: Sep. 6, 2019

(65) Prior Publication Data
US 2021/0048496 A1 Feb. 18, 2021

(30) Foreign Application Priority Data

Mar. 1, 2018 (JP) .............................. JP2018-036934

(51) Int. Cl.
*G01R 33/54* (2006.01)
*G01R 33/36* (2006.01)
(Continued)

(52) U.S. Cl.
CPC ....... *G01R 33/543* (2013.01); *G01R 33/3607* (2013.01); *G01R 33/5608* (2013.01); *A61B 5/055* (2013.01)

(58) Field of Classification Search
CPC ............ G01R 33/3607; G01R 33/5608; G01R 33/543; A61B 5/055
See application file for complete search history.

(56) References Cited

U.S. PATENT DOCUMENTS

2015/0359475 A1\* 12/2015 Bennett .............. G01R 33/5601
600/420
2016/0025834 A1\* 1/2016 Horger ............... G01R 33/5617
324/309
2016/0139222 A1 5/2016 Frydman et al.

FOREIGN PATENT DOCUMENTS

JP 10-277006 10/1998
JP 2002-233515 A 8/2002
(Continued)

OTHER PUBLICATIONS

Extended European Search Report, European Patent Application No. 19761442.3, dated Apr. 21, 2021, thirteen pages.
(Continued)

*Primary Examiner* — Gregory H Curran
(74) *Attorney, Agent, or Firm* — Fenwick & West LLP

(57) ABSTRACT

A nuclear magnetic resonance apparatus (100) includes: a static magnetic field former (10) that forms a static magnetic field; an object holder (2) that holds an object in the static magnetic field; a pulse applicator (51a) that applies π/2 pulse having the Larmor frequency of an atom to be measured to the object in the static magnetic field, and then applies a π pulse having the Larmor frequency to the object at least a predetermined number of times (the predetermined number being two or more) at an interval of the predetermined period, the π pulse being applied for a first time at a
(Continued)

time point at which half the predetermined period has elapsed after applying the π/2 pulse; and a detector (40) that detects the signal intensity of a spin echo signal generated from the object as a result of the last instance of the predetermined number of times of application of the π pulse.

16 Claims, 11 Drawing Sheets

(51) Int. Cl.
    *G01R 33/56*      (2006.01)
    *A61B 5/055*      (2006.01)

(56) References Cited

FOREIGN PATENT DOCUMENTS

| WO | WO 2013/094582 A1 | 6/2013 |
| WO | WO 2016/122810 A1 | 8/2016 |

OTHER PUBLICATIONS

Harms, S.E. et al., "Multiple spin echo magnetic resonance imaging of the brain," *RadioGraphics*, vol. 6, No. 1, Jan. 1, 1986, pp. 117-134.

Nikken, J.J. et al., "MRI of the kidney—state of the art," *European Radiology*, vol. 17, No. 11, Jul. 24, 2007, pp. 2780-2793.

PCT International Search Report (w/ English translation) and Written Opinion, International Application No. PCT/JP2019/008240, dated Apr. 23, 2019, 8 Pages.

European Examination Report, European Patent Application No. 19761442.3, dated Feb. 2, 2022, 12 pages.

Grucker, D. et al., "Chemical and molecular exchange effects on $T_2$ relaxation of living tissues: A pulse spacing dependence study", Biochimica Et Biophysica Acta, Elsevier Science Publishers, Amsterdam, NL, vol. 887, No. 3, Aug. 1, 1986 (Aug. 1, 1986), pp. 249-255, XP023474375, ISSN: 0167-4889, DOI: 10.1016/0167-4889(86)90152-7.

\* cited by examiner

NUCLEAR MAGNETIC RESONANCE APPARATUS, MAGNETIC RESONANCE IMAGING APPARATUS, NUCLEAR MAGNETIC RESONANCE METHOD, MAGNETIC RESONANCE IMAGING METHOD, METHOD FOR DETERMINING MEASUREMENT CONDITIONS, AND PROGRAM

TECHNICAL FIELD

The present disclosure relates to a nuclear magnetic resonance apparatus, a magnetic resonance imaging apparatus, a nuclear magnetic resonance method, a magnetic resonance imaging method, a method for determining a measurement condition, and a program.

BACKGROUND ART

Magnetic resonance imaging (MRI) apparatuses have been known to image the information of the interiors of samples using nuclear magnetic resonance (NMR) phenomena.

Nuclear magnetic resonance occurs in the case of applying a pulse having the same frequency as the frequency of the precession (Larmor frequency) to a nuclear spin precessing about a static magnetic field direction as an axis. A sample image generated based on a response signal, obtained by applying such a pulse to a sample, from the nuclear spin of the nucleus included in the sample, in response to the pulse, is referred to as an MRI image. For example, the characteristics of a relaxation phenomenon in which a nuclear spin of which the state is changed by resonance is restored to the former state thereof depend on the situation of the nuclear spin. Thus, an MRI image can be obtained by imaging a nuclear magnetization distribution, based on such a relaxation phenomenon, by an MRI apparatus.

Such a relaxation phenomenon is divided into longitudinal relaxation according to a component in the static magnetic field direction (Z direction) of a nuclear spin and transverse relaxation according to a component in the rotation direction (XY direction) of the nuclear spin. The longitudinal relaxation and the transverse relaxation are also referred to as T1 relaxation and T2 relaxation on the basis of the time constants of respective functions thereof Examples of conventional MRI apparatuses include an MRI apparatus by which $\pi/2$ pulse (90° pulse) as an excitation pulse and a $\pi$ pulse (180° pulse) as a reverse pulse are applied at intervals of a predetermined period $\tau$, like a pulse train illustrated in FIG. 10, and T1-weighted image obtained by imaging a nuclear magnetization distribution provided with a contrast by longitudinal relaxation and a T2-weighted image obtained by imaging a nuclear magnetization distribution provided with a contrast by transverse relaxation are obtained based on a Hahn echo (spin echo) further observed after a lapse of $\tau$ (for example, Patent Literature 1). However, since it is demanded to primarily set imaging time at practical time, it is not common to acquire an image on the basis of T1 weighting.

CITATION LIST

Patent Literature

Patent Literature 1: Unexamined Japanese Patent Application Kokai Publication No. H10-277006

SUMMARY OF INVENTION

Technical Problem

The conventional spin echo method based on the pulse train illustrated in FIG. 10 has a problem that a clear MRI image is unable to be obtained depending on the kind of a component included in a sample. For example, in a case in which the sample is the kidney, the conventional spin echo method has been incapable of obtaining an MRI image with a clear contrast because the respective time constants T2 (obtained by a Hahn echo method described below) of the kidney tissue, the ureter, and blood as the major components of the kidney have exhibited similar behavior.

FIG. 11 illustrates spin echo intensity characteristics based on the conventional method in a case in which a sample mimics the kidney. In the figure, "gel" "urine", and "saline solution" correspond to the kidney tissue, the ureter, and blood (vessel), respectively, among the components of the kidney. As can be seen from the figure, it is shown that the conventional Hahn echo method results in insignificant differences in the signal intensity of a spin echo between the components (the intensities of the three objects are almost equal to each other in both TE1 and TE2), and is therefore incapable of obtaining a clear MRI image.

Likewise, it has been also difficult that a conventional NMR apparatus that detects an NMR signal from a tissue sample distinctly discriminates a component included in such a sample as described above.

The present disclosure was made under such actual circumstances with an objective to provide a nuclear magnetic resonance apparatus, a magnetic resonance imaging apparatus, a nuclear magnetic resonance method, a magnetic resonance imaging method, a method for determining a measurement condition, and a program, in which a contrast is provided between nuclear magnetic resonance signals.

Solution to Problem

A nuclear magnetic resonance apparatus according to a first aspect of the present disclosure includes:
  a static magnetic field former that forms a static magnetic field;
  an object holder that holds an object in the static magnetic field;
  a pulse applicator that applies $\pi/2$ pulse having a Larmor frequency of an atom to be measured to the object in the static magnetic field and then applies a $\pi$ pulse having the Larmor frequency to the object at least a predetermined number of times (the predetermined number being two or more) at an interval of the predetermined period, the $\pi$ pulse being applied for a first time at a time point at which half the predetermined period has elapsed after applying the $\pi/2$ pulse; and
  a detector that detects a signal intensity of a spin echo signal generated from the object as a result of a last instance of the predetermined number of times of application of the $\pi$ pulse.

The nuclear magnetic resonance apparatus according to the first aspect may be a nuclear magnetic resonance apparatus capable of discriminating a first component and a second component in the object from each other, and capable of detecting the first component and the second component,
  wherein, in a case in which: the $\pi/2$ pulse is applied to the first component in the static magnetic field and then the $\pi$ pulse is applied to the first component at least the predetermined number of times at an interval of the predetermined period, the π pulse being applied for a first time at a time point at which half the predetermined period has elapsed after applying the π/2 pulse; a signal intensity of a spin echo signal generated from the first component as a result of a last instance of the predetermined number of times of the application of the π pulse is regarded as a first signal intensity; the π/2 pulse is applied to the second component in the static magnetic field and then the π pulse is applied to the second component at least the predetermined number of times at an interval of the predetermined period, the π pulse being applied for a first time at a time point at which half the predetermined period has elapsed after applying the π/2 pulse; and a signal intensity of a spin echo signal generated from the second component as a result of a last instance of the predetermined number of times of the application of the π pulse is regarded as a second signal intensity, the predetermined period and the predetermined number of times are set so that a value obtained by dividing a higher one of the first signal intensity and the second signal intensity by a lower one of the first signal intensity and the second signal intensity is not less than a predetermined value.

The pulse applicator may be a pulse applicator in which it is possible to change the predetermined period in a range of 5 μs or more and 1 s or less.

A magnetic resonance imaging apparatus according to a second aspect of the present disclosure includes:

the nuclear magnetic resonance apparatus according to the first aspect of the present disclosure; and an image generator that generates an image based on the signal intensity detected by the detector.

A nuclear magnetic resonance method according to a third aspect of the present disclosure includes:

a step of applying π/2 pulse having a Larmor frequency of an atom to be measured to an object in a static magnetic field, and then applying a π pulse having the Larmor frequency to the object at least a predetermined number of times (the predetermined number being two or more) at an interval of the predetermined period, the π pulse being applied for a first time at a time point at which half the predetermined period has elapsed after applying the π/2 pulse; and a step of detecting a signal intensity of a spin echo signal generated from the object as a result of a last instance of the predetermined number of times of application of the π pulse.

A magnetic resonance imaging method according to a fourth aspect of the present disclosure includes:

a step of generating an image of the object based on the signal intensity detected by the nuclear magnetic resonance method according to the third aspect of the present disclosure.

A program according to a fifth aspect of the present disclosure allows a computer to function as:

pulse application means that allows a pulse applicator to apply π/2 pulse having a Larmor frequency of an atom to be measured to an object in a static magnetic field, and then apply a π pulse having the Larmor frequency to the object at least a predetermined number of times (the predetermined number being two or more) at an interval of the predetermined period, the π pulse being applied for a first time at a time point at which half the predetermined period has elapsed after applying the π/2 pulse; and detection means that allows a detector to detect a signal intensity of a spin echo signal generated from the object as a result of a last instance of the predetermined number of times of application of the π pulse.

It is also acceptable to allow the computer to further function as image generation means that generates an image of the object based on the signal intensity.

A method for determining a measurement condition according to a sixth aspect of the present disclosure is a method for determining a measurement condition including a predetermined period and/or a predetermined number of times in a nuclear magnetic resonance method including: applying a π/2 pulse having a Larmor frequency of an atom to be measured to an object in a static magnetic field and then applying a π pulse having the Larmor frequency to the object at least the predetermined number of times (the predetermined number being two or more) at an interval of the predetermined period, the π pulse being applied for a first time at a time point at which half the predetermined period has elapsed after applying the π/2 pulse; and detecting a signal intensity of a spin echo signal generated from the object as a result of a last instance of the predetermined number of times of application of the π pulse, wherein, in a case in which: one or more candidate periods are candidates for the predetermined period; and one or more candidate numbers of times are candidates for the predetermined number of times, the method for determining a measurement condition includes:

a first pulse application step of, for each of the candidate periods, applying the π/2 pulse to a first reference object in the static magnetic field and then applying the π pulse to the first reference object at least a greatest number of the candidate numbers of times at an interval of the candidate period, the π pulse being applied for a first time at a time point at which half the candidate period has elapsed after applying the π/2 pulse;

a first signal detection step of, for each of the candidate numbers of times, detecting, as a first signal intensity, a signal intensity of a spin echo signal generated from the first reference object by applying the π pulse as a result of a last instance of the candidate number of times in the first pulse application step;

a second pulse application step of, for each of the candidate periods, applying the π/2 pulse to a second reference object in the static magnetic field and then consecutively applying the π pulse to the second reference object at least the greatest number of the candidate numbers of times at an interval of the candidate period, the π pulse being applied for a first time at a time point at which half the candidate period has elapsed after applying the π/2 pulse;

a second signal detection step of, for each of the candidate numbers of times detecting, as a second signal intensity, a signal intensity of a spin echo signal generated from the second reference object by applying the π pulse as a result of a last instance of the candidate number of times in the second pulse application step; and a condition determination step of, for each of the candidate periods and for each of the candidate numbers of times, determining the candidate period as one of the predetermined periods and/or determining the candidate number of times as one of the predetermined numbers of times in a case in which a value obtained by dividing the first signal intensity by the second signal intensity is not less than a predetermined value, with regard to the first signal intensity corresponding to the application of the π pulse as the result of the last instance of the candidate number of times in the first pulse application step performed at an interval of the candidate period and the second signal intensity corresponding to the application of the π pulse as the result of the last instance of the candidate number of times in the second pulse application step performed at an interval of the candidate period, at intervals of the candidate period and the candidate number of times.

A program according to a seventh aspect of the present disclosure is a program that determines a measurement condition including a predetermined period and/or a predetermined number of times in a nuclear magnetic resonance method including: allowing a pulse applicator to apply a π/2 pulse having a Larmor frequency of an atom to be measured to an object in a static magnetic field and then apply a π pulse having the Larmor frequency to the object at least the predetermined number of times (the predetermined number being two or more) at an interval of the predetermined period, the π pulse being applied for a first time at a time point at which half the predetermined period has elapsed after applying the π/2 pulse; and allowing a detector to detect a signal intensity of a spin echo signal generated from the object as a result of a last instance of the predetermined number of times of application of the π pulse, wherein, in a case in which: one or more candidate periods are candidates for the predetermined period; and one or more candidate numbers of times are candidates for the predetermined number of times, the program allows a computer to function as:

first pulse application means that allows the pulse applicator to, for each of the candidate periods, apply the π/2 pulse to a first reference object in the static magnetic field and then apply the π pulse to the first reference object at least a greatest number of the candidate numbers of times at an interval of the candidate period, the π pulse being applied for a first time at a time point at which half the candidate period has elapsed after applying the π/2 pulse;

first signal detection means that allows the detector to, for each of candidate numbers of times, detect, as a first signal intensity, a signal intensity of a spin echo signal generated from the first reference object by applying the π pulse as a result of a last instance of the candidate number of times in the first pulse application means;

second pulse application means that allows the pulse applicator to, for each of the candidate periods, apply the π/2 pulse to a second reference object in the static magnetic field at an interval of the candidate period and then apply the π pulse to the second reference object at least the greatest number of the candidate numbers of times at an interval of the candidate period, the π pulse being applied for a first time at a time point at which half the candidate period has elapsed after applying the π/2 pulse;

second signal detection means that allows the detector to, for each of the candidate numbers of times, detect, as a second signal intensity, a signal intensity of a spin echo signal generated from the second reference object by applying the π pulse as a result of a last instance of the candidate number of times in the second pulse application means; and condition determination means that, for each of the candidate periods and for each of the candidate numbers of times, determines the candidate period as one of the predetermined periods and/or determines the candidate number of times as one of the predetermined numbers of times in a case in which a value obtained by dividing the first signal intensity by the second signal intensity is not less than a predetermined value, with regard to the first signal intensity corresponding to the application of the π pulse as the result of the last instance of the candidate number of times in the first pulse application means performed at an interval of the candidate period and the second signal intensity corresponding to the application of the π pulse as the result of the last instance of the candidate number of times in the second pulse application means performed at an interval of the candidate period.

Advantageous Effects of Invention

In accordance with the present disclosure, a contrast can be obtained between nuclear magnetic resonance signals.

DESCRIPTION OF EMBODIMENTS

One embodiment of the present disclosure will be described with reference to the drawings.

(Configuration of MRI Apparatus 100)

Figure 1:
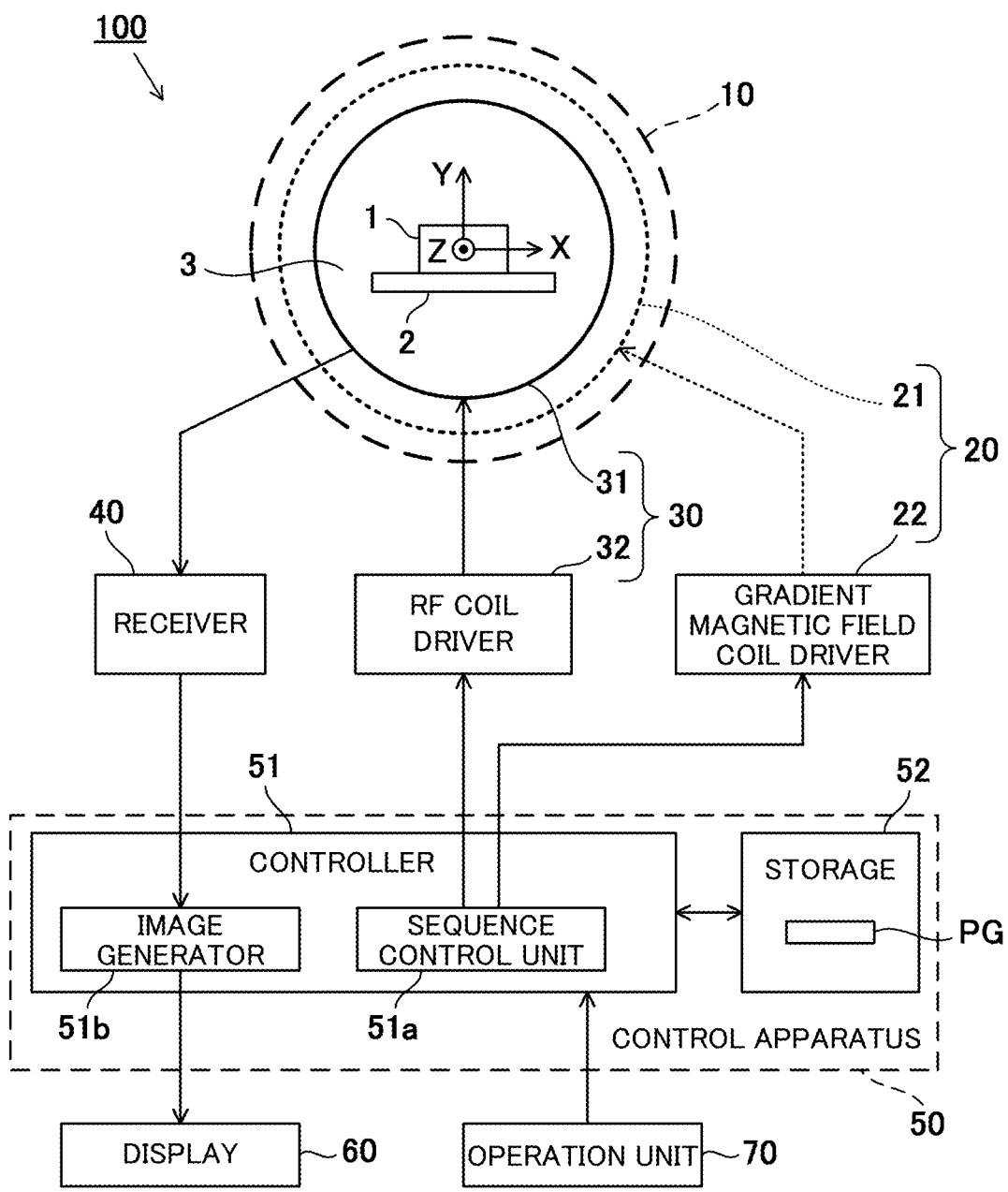
FIG. 1 is a block diagram illustrating the configuration of an MRI apparatus according to one embodiment of the present disclosure.

As illustrated in FIG. 1, an MRI apparatus 100 according to one embodiment of the present disclosure includes a static magnetic field coil 10, a gradient magnetic field generator 20, a pulse applicator 30, a receiver 40, a control apparatus 50, a display 60, and a operation unit 70.

The static magnetic field coil 10, a gradient magnetic field coil 21 included in the gradient magnetic field generator 20, and a radio frequency (RF) coil 31 included in the pulse applicator 30 are placed about, for example, the same axis (Z axis), and disposed in a housing which is not illustrated. A sample 1 to be photographed is mounted on a mount stage 2, and moved in a bore 3 (examination space) formed in the housing depending on a site to be photographed by conveying means which is not illustrated.

The static magnetic field coil 10 forms a uniform static magnetic field in the bore 3. The formed static magnetic field is a horizontal magnetic field generally parallel to the Z direction. The static magnetic field coil 10 includes, for example, a superconducting coil or a normal conducting coil, and driven under the control of the control apparatus 50 through a static magnetic field coil driver which is not illustrated. The static magnetic field coil 10 may be drivingly controlled by a control system independent of the control apparatus 50. A configuration in which the static magnetic field is generated is not limited to the superconducting coil and the normal conducting coil, and, for example, a permanent magnet may be used as the configuration.

The gradient magnetic field generator 20 generates a gradient magnetic field necessary for imaging in the bore 3, and includes the gradient magnetic field coil 21 and a gradient magnetic field coil driver 22 that drives the gradient magnetic field coil 21.

The gradient magnetic field coil 21 generates gradient magnetic fields in which static magnetic field intensity formed by the static magnetic field coil 10 is allowed to be gradient in triaxial directions orthogonal to each other. The gradient magnetic fields in the triaxial directions orthogonal to each other are used as a slice gradient magnetic field Gs in a slice axis direction, a phase encoding gradient magnetic field Gp in a phase axis direction, and a frequency encoding gradient magnetic field Gr in a frequency axis direction, respectively. The slice gradient magnetic field Gs is a gradient magnetic field for slice selection. The phase encoding gradient magnetic field Gp and the frequency encoding gradient magnetic field Gr are gradient magnetic fields for measuring the spatial distribution of a resonance element. The gradient magnetic field coil 21 includes a three-system coil in order to generate such gradient magnetic fields.

The gradient magnetic field coil driver 22 supplies a driving signal to the gradient magnetic field coil 21 to generate gradient magnetic fields under the control of the control apparatus 50. The gradient magnetic field coil driver 22 includes a three-system drive circuit, which is not illustrated, in accordance with the three-system coil included in the gradient magnetic field coil 21.

Any axis of X-, Y-, and Z-axes orthogonal to each other in a static magnetic field space can be allowed to be a slice axis. In the present embodiment, the Z-axis direction which is the direction normal to the paper face in FIG. 1 is allowed to be the slice axis, one of the remaining axes is allowed to be a phase axis, and the other is allowed to be a frequency axis. The slice axis, the phase axis, and the frequency axis can also be allowed to have optional inclinations while keeping orthogonality to each other.

The pulse applicator 30 is intended to apply an RF pulse for generating nuclear magnetic resonance to the sample 1, and includes the RF coil 31 and an RF coil driver 32 that drives the RF coil 31.

The RF coil 31 forms a high frequency magnetic field for exciting the nuclear spin of the sample 1 in a static magnetic field space. Such formation of a high frequency magnetic field is also referred to as application or transmission of an RF pulse. The RF coil 31 has the function of receiving a magnetic resonance (MR) signal which is an electromagnetic wave generated by excited nuclear spin as well as the function of transmitting an RF pulse. The MR signal includes a spin echo signal. A coil for transmitting an RF pulse and a coil for receiving an MR signal can also be separately configured.

The RF coil driver 32 supplies a driving signal to the RF coil 31 to drive the RF coil 31 under the control of the control apparatus 50. Specifically, the RF coil driver 32 generates, in the RF coil 31, an RF pulse corresponding to a Larmor frequency depending on the kind of an atom to be measured and on magnetic field intensity. The pulse applicator 30, configured as described above, particularly applies "specific pulse train" described later to the sample 1.

The receiver 40 is connected to the RF coil 31, and detects an MR signal received by the RF coil 31. The receiver 40 digitally converts the detected MR signal, and transmits the MR signal to the control apparatus 50.

The control apparatus 50 includes a computer that controls the entire operation of the MRI apparatus 100, and a sequencer that drives the RF coil driver 32 and the gradient magnetic field coil driver 22 with a predetermined pulse train (pulse sequence), as well as includes a controller 51 and a storage 52.

The controller 51 includes a central processing unit (CPU), a field-programmable gate array (FPGA), an application specific integrated circuit (ASIC), and the like, and executes an operation program stored in the storage 52, to control the operation of each unit of the MRI apparatus 100.

The storage 52 includes a read only memory (ROM), a random access memory (RAM), and the like, and stores the data of various operation programs (including a program PG1 for executing image generation processing described later and a program PG2 for executing focus condition determination processing described later), table data described later, and the like, in advance. The RAM of the storage 52 temporarily stores data indicating various operation results, data indicating determination results, and the like.

The controller 51 includes a pulse controller 51a and an image generator 51b as function units.

The pulse controller 51a drivingly controls the gradient magnetic field generator 20 and the pulse applicator 30 on the basis of pulse train data indicating an RF pulse including a specific pulse train described later, as well as the pulse trains of the slice gradient magnetic field Gs, the phase encoding gradient magnetic field Gp, and the frequency encoding gradient magnetic field Gr. The pulse train data may be stored in the storage 52 in advance, or may be able to be input and reset by user manipulation through the operation unit 70 described later.

Particularly, in this embodiment, the pulse controller 51a drivingly controls the pulse applicator 30, and allows the following specific pulse train (for example, a pulse train illustrated in FIG. 2) to be applied to the sample 1. Specifically, $\pi/2$ pulse (90° pulse, excitation pulse) is applied, and a $\pi$ pulse (180° pulse, reverse pulse) is then applied after a lapse of time $\tau$. Once the $\pi$ pulse is applied, a $\pi$ pulse is then consecutively applied at intervals of time $2\tau$. A pulse train in which a $\pi$ pulse is applied plural times at intervals of $2\tau$ after application of $\pi/2$ pulse in such a manner is referred to as "specific pulse train".

The $\pi/2$ pulse and $\pi$ pulse described above are RF pulses corresponding to a Larmor frequency depending on the kind of an atom to be measured and on magnetic field intensity. Such an RF pulse is a pulse obtained by cutting a radio wave having a Larmor frequency into a pulse form by pulse modulation, and makes the atomic nucleus of an object rotate in an appropriate static magnetic field. A $\pi/2$ pulse (90° pulse) is an RF pulse at a rotation angle of 90° while a π pulse (180° pulse) is an RF pulse at a rotation angle of 180°. The Larmor frequencies of the π/2 pulse and then π pulse are equal to each other.

In accordance with a specific pulse train, a spin echo is generated as an MR signal, every application of the π pulse, between the application and 2τ. A relationship of τ=TE/2 is satisfied between time τ and echo time TE from the application of the π/2 pulse to the sample 1 to the detection of the first spin echo (spin echo generated by applying the first π pulse).

The reason why such a characteristic specific pulse train as described above is applied to the sample 1 will be described.

As explained in the description of the problems, the conventional spin echo method has had a problem that it is impossible to obtain a clear MRI image depending on the kind of a component included in a sample.

Figure 11:
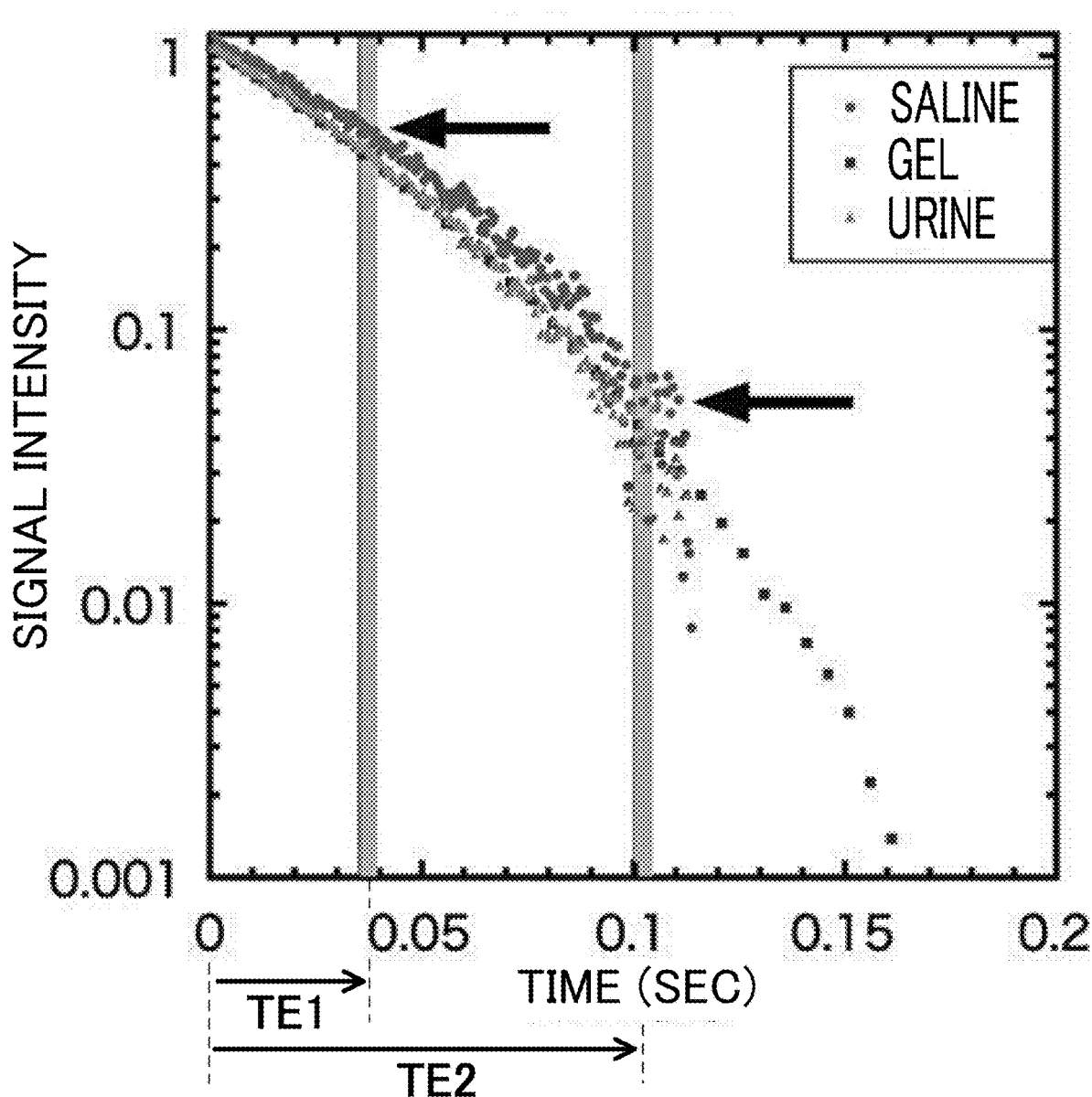
FIG. 11 is a diagram of a graph indicating time for which a pulse is applied with the pulse train according to the conventional example, and the signal intensity of a spin echo.

For example, the problem will be described with reference to a case in which a sample mimics the kidney. As illustrated in FIG. 11, in a case in which the intensity of a spin echo signal generated by application of a reverse pulse is plotted with respect to time from application of an excitation pulse to acquisition of the spin echo signal by a Hahn echo method with $^{23}$Na to be measured, with regard to each component, using "gel" corresponding to the kidney tissue, "urine" corresponding to the ureter, and "saline solution" corresponding to blood, as a model for the components of the kidney, all the components exhibit the similar damping curves of the signal intensities of spin echoes (hereinafter, also referred to as "spin echo intensity"). There is no noticeable difference in spin echo intensity between the mimic tissues described above.

As a result of intensive research, the present inventor found that the signal intensities of a plurality of spin echoes generated by application of the respective π pulses in the case of applying a specific pulse train to a sample exhibit damped oscillation, the damped oscillation exhibits a pattern depending on (a) the kind of the component of the sample and (b) an interval 2τ of application of pulses in the specific pulse train, and particularly, (c) the damped oscillation pattern of spin echo intensity derived from a different component tends not to necessarily fluctuate in a linking manner but to exhibit a different fluctuation according to each component in the case of varying the interval 2τ of the application of the pulses in the specific pulse train. In addition, it was found that utilization of such characteristics enables obtainment of such a combination of the damped oscillation patterns of the components of a sample that a specific component in the sample can be discriminated from the other components on the basis of spin echo intensity by variously changing an interval 2τ of application of pulses in a specific pulse train.

Figure 6:
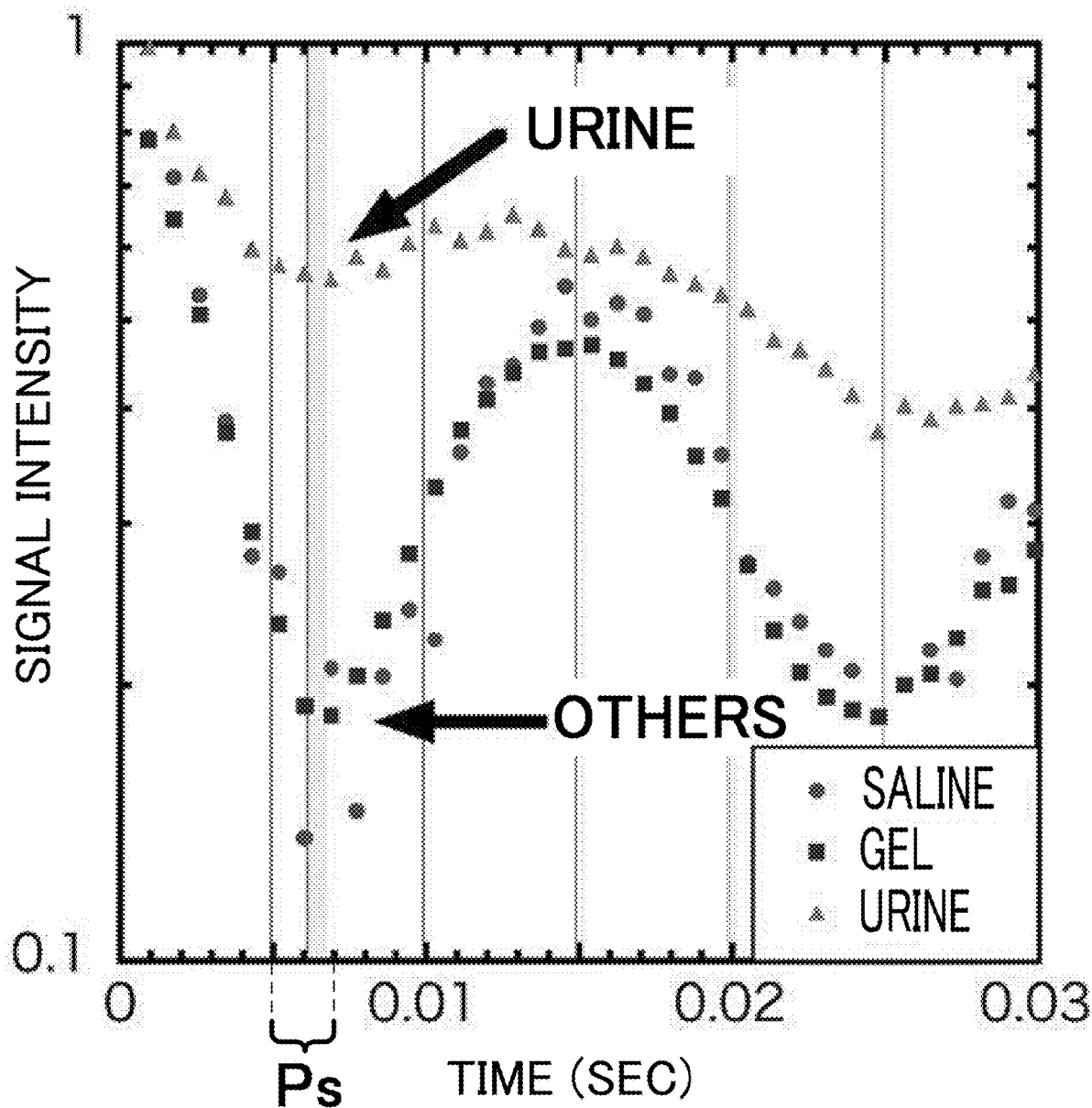
FIG. 6 is a diagram of a graph indicating spin echo intensity in the case of applying a specific pulse train to saline solution, gel, and urine with $^{23}$Na as an atom to be measured.

A specific example of the characteristics will be described with reference to FIG. 6. FIG. 6 is a graph of spin echo intensity characteristics in the case of applying the specific pulse train illustrated in FIG. 2 to each component using "gel" corresponding to the kidney tissue, "saline solution" corresponding to blood, and "urine" corresponding to the ureter, as a model for the components of the kidney. The abscissa of the graph indicates an elapsed time from start of π/2 pulse while the ordinate of the graph indicates the signal intensity of a spin echo generated by application of each π pulse.

Referring now to FIG. 6, first, it is found that the damped oscillation of the spin echo intensities of all the components occurs. Although the damped oscillation patterns of the spin echo intensities of "saline solution" and "gel" are similar to each other, these damped oscillation patterns are different from the damped oscillation pattern of the spin echo intensity of "urine". As is apparent from FIG. 6, therefore, comparison for appropriate elapsed time enables "urine", and "saline solution" and "gel" to be discriminated from each other on the basis of spin echo intensities. For example, comparison in a period indicated by "Ps" (corresponding to one spin echo by application of the seventh π pulse) in FIG. 6 shows that a phenomenon occurs that the spin echo intensity of "urine" is several times or more the spin echo intensities of "saline solution" and "gel". In other words, it is found that generation of an MRI image with a clear contrast, which has been impossible with the use of a conventional spin echo method (see FIG. 11), is enabled by experientially determining a combination of an interval of application of the pulses of a specific pulse train and a period of acquisition of a spin echo (hereinafter, also referred to as "focus condition"), in which the phenomenon noticeably occurs.

For example, an MRI image with a positive contrast which is the weighted contrast of "urine" of which the spin echo intensity is higher than those of "saline solution" and "gel" (an image in which the ureter tissue of the mimic kidney is weighted) can be obtained by applying a specific pulse train to samples of "urine", "saline solution", and "gel" at various pulse application intervals by the MRI apparatus 100, experientially determining, in advance, a combination of an interval of application of the pulses of a specific pulse train (hereinafter, "specific interval Ts") and a spin echo acquisition period across the signal of one spin echo (hereinafter, "specific period Ps"), in which the spin echo intensity of "urine" is predetermined times (in a case in which the predetermined times are a times, greater a is more preferred, and at least α≥2 is acceptable) or more the spin echo intensities of "saline solution" and "gel", and then applying a specific pulse train at a pulse application interval 2τ set at the specific interval Ts to the mimic kidney in which "saline solution", "gel", and "urine" coexist by the MRI apparatus 100, to generate an image on the basis of the intensity of a spin echo detected in the specific period Ps.

Not only the MRI image with a positive contrast but also an image with a negative contrast can be obtained. For example, an MRI image with a negative contrast which is the weighted contrast of "saline solution" of which the spin echo intensity is lower than those of "urine" and "gel" (the spin echo intensity of "saline solution" is 1/α time or less those of the other components) (an image in which the blood or vessel of the mimic kidney is weighted) can be obtained by applying a specific pulse train to samples of "urine", "saline solution", and "gel" at various pulse application intervals by the MRI apparatus 100, experientially determining, in advance, a combination of a specific interval Ts and a specific period Ps, in which the spin echo intensities of "urine" and "gel" is predetermined times (in a case in which the predetermined times are α times, greater α is more preferred, and at least α≥2 is acceptable) or more the spin echo intensity of "saline solution", and then applying a specific pulse train at a pulse application interval 2τ set at the specific interval Ts to the mimic kidney in which "saline solution", "gel", and "urine" coexist by the MRI apparatus 100, to generate an image on the basis of the intensity of a spin echo detected in the specific period Ps.

Referring back to FIG. 1, the pulse controller 51a controls the π pulse interval 2τ of the specific pulse train in a variable manner, and allows the pulse applicator 30 to apply the specific pulse train in the specific interval Ts, experientially determined in advance. Specifically, table data, in which a component to be weighted, expected to be included in the sample 1, and the specific interval Ts and the specific period Ps, in which the component can be discriminated from the other components on the basis of a spin echo signal (the component is weighted in an MRI image), and which has been experientially determined in advance, are associated with each other, is stored in the ROM of the storage 50, and the pulse controller 51*a* controls the specific pulse train so that a π pulse is applied for predetermined application time (for example, until at least the specific period Ps elapses) at the specific interval Ts according to the component intended to be weighted, determined by input from a user, or the like, with reference to the table data.

The pulse controller 51*a* is configured to be able to control the π pulse interval 2τ of the specific pulse train to the specific interval Ts according to the component intended to be weighted. The pulse controller 51*a* may be configured to be able to control the π pulse interval 2τ, for example, in a range of 5 μs or more and 1 s or less, for example, in increments of 0.1 to 1 μs (preferably, increments of 0.1 μs), in a variable manner.

Figure 2:
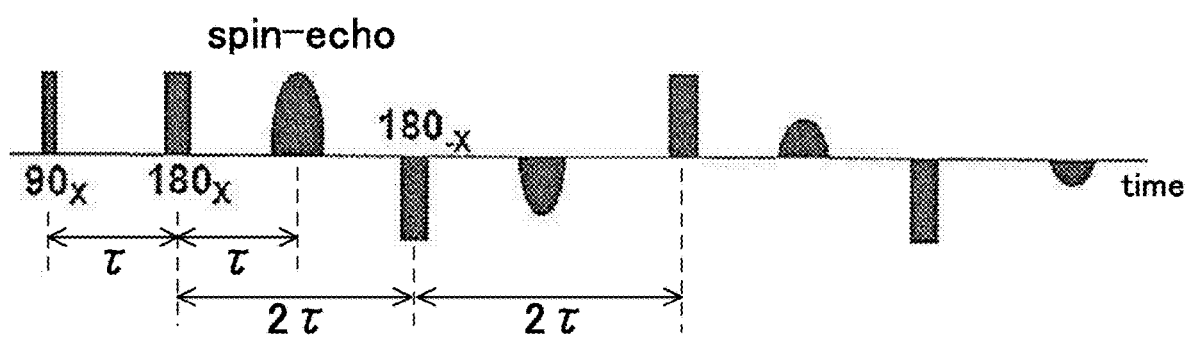
FIG. 2 is a diagram illustrating a specific pulse train according to one embodiment of the present disclosure.
Figure 3:
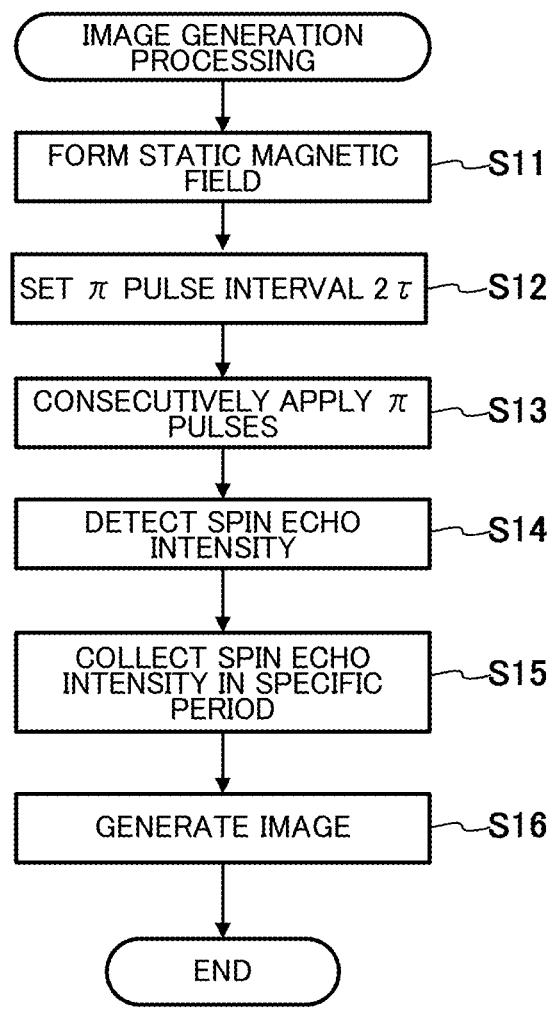
FIG. 3 is a flow chart of image generation processing according to one embodiment of the present disclosure.
Figure 4:
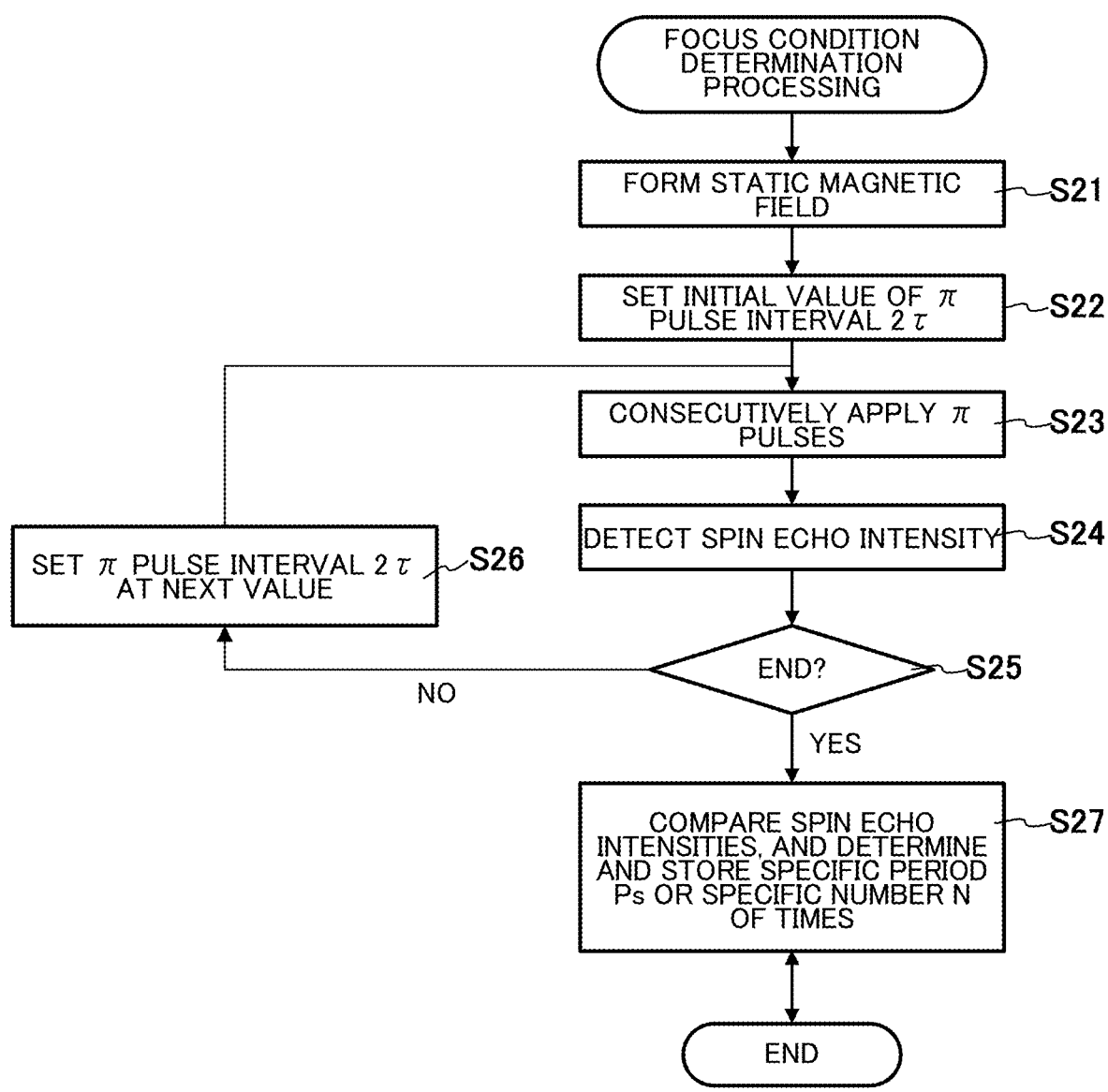
FIG. 4 is a flow chart of focus condition determination processing according to one embodiment of the present disclosure.

In the case of allowing the pulse applicator 30 to transmit the specific pulse train, the pulse controller 51*a* may allow the pulse applicator 30 to consecutively transmit π pulses having the same polarity (pulse train referred to as Carr-Purcell-Meiboom-Gill (CPMG)), or preferably allows the pulse applicator 30 to alternately transmit π pulses having opposite polarities (referred to as alternating polarity Carr Purcell (APCP); S. Watanabe and S. Sasaki. J. Jpn. Appl. Phys. Express Lett. (2003)), as illustrated in FIG. 2. This is because consecutive transmission of π pulses having the same polarity can allow a spin echo detected between π pulses to overlap a spin echo detected between the next π pulses on a time axis, thereby resulting in the deterioration of detection accuracy.

The image generator 51*b* allows the storage 52 to store the data of an MR signal collected by the receiver 40. The MR signal acquired by the image generator 51*b* is a signal in Fourier space. The image generator 51*b* biaxially encodes the MR signal on the basis of the gradients of the phase encoding gradient magnetic field Gp and the frequency encoding gradient magnetic field Gr. Accordingly, the MR signal is obtained as a signal in two-dimensional Fourier space (k-space). The phase encoding gradient magnetic field Gp and the frequency encoding gradient magnetic field Gr determine the sampling position of a signal in k-space. The image generator 51*b* performs the two-dimensional Fourier transform of data in k-space to decompose the data into a signal at each position, thereby generating an MRI image with light and shade proportional to the nuclear magnetization of each position.

Particularly, in this embodiment, the image generator 51*b* acquires a spin echo signal from the receiver 40, and detects the intensity of the spin echo. The image generator 51*b* acquires a specific period Ps corresponding to a component intended to be weighted, determined by input from a user, or the like, with reference to the table data prepared in the ROM in advance, as described above. The image generator 51*b* determines whether or not the specific period Ps is achieved from the start of the application of a specific pulse train, and allows the storage 52 to store the spin echo intensity obtained from the sample 1 during the specific period Ps in a case in which the specific period Ps is achieved. The image generator 51*b* generates an MRI image, and allows the display 60 to display the generated MRI image. A contrast that enables a specific component and the other components to be distinctly discriminated from each other is generated in the MRI image obtained in such a manner.

Specifically, for example, the mimic kidney in which "saline solution", "gel", and "urine" coexist is measured as the sample 1, an application interval 2τ of a specific pulse train is controlled in a specific interval Ts suitable for observing urine by control by the pulse controller 51*a* in a case in which a component intended to be weighted is set at "urine", and the sample 1 is irradiated with such a specific pulse train as illustrated in FIG. 2. The image generator 51*b* detects spin echo intensities in a specific period Ps set, in advance, as a period suitable for observing urine. In the spin echo intensities detected in the specific period Ps, the spin echo intensity derived from "urine" is high to such a degree that the spin echo intensity is distinguishable from the spin echo intensities derived from "saline solution" and "gel". The controller 51 generates an MRI image according to a spin echo intensity based on each coordinate space by subjecting the MR signal acquired in the specific period Ps to fast Fourier transform by the image generator 51*b* while applying a gradient magnetic field in a manner, in which the magnitude of the gradient magnetic field is pulsingly varied, by the pulse controller 51*a*. As a result, it is possible to obtain the MRI image with a positive contrast in which "urine" of which the intensity is several times those of the other components is represented.

The spin echo intensities acquired in the image generator 51*b* may be normalized with respect to a reference spin echo intensity. For example, the spin echo intensity corresponding to each pixel obtained from the sample 1 may be normalized based on the maximum value of the spin echo intensities, or may be normalized based on a spin echo intensity measured together with the sample 1 and obtained from a reference sample having a predetermined concentration and including an atom to be measured.

The spin echo intensities acquired in the image generator 51*b* may be normalized by another method. For example, it is acceptable to acquire spin echo signals not only over the specific period Ps but also over a predetermined period Ps' (for example, an overall period in which pulses are applied) in the period in which the pulses are applied, and to normalize the spin echo intensity of a certain pixel acquired in the predetermined period Ps with respect to a value indicated at time zero by a damped oscillation function fitted to a plurality of spin echo intensities acquired over the predetermined period Ps' in the pixel. Due to the normalization in such a manner, it is possible to more distinctly distinguish which pixel belongs to any of components (for example, "saline solution", "gel", or "urine" in the mimic kidney) in the image derived from the sample 1 on the basis of the damped oscillation pattern of each component.

The display 60 includes a liquid crystal display (LCD), an organic electroluminescent display (OELD), or the like, and displays the MRI image generated by the image generator 51*b*.

The operation unit 70 accepts manipulation by a user, and supplies a manipulate signal according to the accepted manipulation to the control apparatus 50. The operation unit 70 includes, for example, a keyboard including a pointing device, a touch panel integrated with the display 60, or the like. For example, the MRI apparatus 100 is configured so that a user can perform determination of a specific component to be observed in the sample 1, or input of pulse train data, by manipulation from the operation unit 70.

Although the specific period Ps is set to acquire one spin echo signal in the configuration described above, the specific period Ps may be set to acquire two or more spin echo signals. In this case, it is also acceptable to apply phase encoding pulses to a plurality of spin echoes generated in the specific period Ps by the pulse controller 51*a* in order to give an S/N ratio, and to use the signal intensity of an integrated signal for generating an MRI image.

Although timing at which a spin echo is acquired is specified based on a specific period Ps in the configuration described above, it is also acceptable to specify the timing on the basis of the number of times of application of a $\pi$ pulse. For example, when a spin echo is generated in a specific period Ps by the n-th application of a $\pi$ pulse in the case of applying a $\pi$ pulse the specific number n of times (n is a natural number of 2 or more) at a specific interval Ts, table data in which a component to be weighted, and a specific interval Ts and the specific number n of times, in which the component can be discriminated from the other elements on the basis of spin echo intensities, are associated with each other is stored in the ROM of the storage 50, and the pulse controller 51*a* controls a specific pulse train so that a $\pi$ pulse is applied at least the specific number n of times at the specific interval Ts according to the component intended to be weighted with reference to the table data, and applies a phase encoding pulse to the spin echo generated by the n-th application of the $\pi$ pulse. When a certain component can be discriminated from the other components on the basis of spin echo signal intensities even after n-th and before n+m-th (m is a natural number of 1 or more) application of a $\pi$ pulse in the case of applying a specific pulse train at a specific interval Ts corresponding to the certain component, it is also acceptable to apply the $\pi$ pulse at least n+m times in order to give an SN ratio, to apply a phase encoding pulse to a plurality of spin echoes generated by the n-th to n+m-th application of the $\pi$ pulses, and to use the signal intensity of an integrated signal for generating an MRI image.

The experientially determined specific interval Ts and specific period Ps (or the specific number n of times) are freely selected as long as being in combination in which a component intended to be weighted and the other components can be discriminated from each other on the basis of spin echo signal intensities. For example, the specific interval Ts and the specific period Ps (or the specific number n of times) may be in combination in which a difference between the signal intensity of the spin echo of the component intended to be weighted and the signal intensities of the spin echoes of the other components can be considered to be prominently large. For example, the specific interval Ts and specific period Ps (or the specific number n of times) may be in combination in which (i) a ratio between the signal intensity of the spin echo of a component intended to be weighted and the signal intensity of at least any spin echo of the other plural components (a value obtained by dividing the higher intensity by the lower intensity) is the highest, or (ii) a ratio between the signal intensity of the spin echo of a component intended to be weighted and the average of the signal intensities of the spin echoes of the other plural components (a value obtained by dividing the higher intensity by the lower intensity) is the highest, within predetermined application time from the start of the application of a specific pulse train. The specific interval Ts and the specific period Ps (or the specific number n of times) may be in combination in which a ratio between the signal intensity of the spin echo of a component intended to be weighted and the signal intensity of the spin echo of another component (a value obtained by dividing the higher intensity by the lower intensity) is predetermined times (for example, at least 2 times) or more, within predetermined application time from the start of the application of a specific pulse train. The specific interval Ts and the specific period Ps (or the specific number n of times) may be in combination in which a ratio between the average of the signal intensities of the plural specific spin echoes of a component intended to be weighted and the average of the signal intensities of the plural specific spin echoes of another component (a value obtained by dividing the higher average by the lower average) is predetermined times (for example, at least 2 times) or more, within predetermined application time from the start of the application of a specific pulse train. Although cases in which the component intended to be weighted is one are described above, components intended to be weighted may be plural. In such a case, the specific interval Ts and the specific period Ps (or the specific number n of times) may be determined so as to be in combination in which the plural components to be weighted and the other component can be discriminated based on spin echo signal intensities. For example, in the case of determining a contrast ratio (a value obtained by dividing one with the higher signal intensity by the other with the lower signal intensity), the average value of the signal intensities of plural components to be weighted and the average value of the signal intensities of the other plural components may be used for computing the contrast ratio; in a case in which the minimum value of the spin echo intensities of the plural components to be weighted is higher than the maximum value of the spin echo intensities of the other plural components, the minimum value and the maximum value may be used for computing the contrast ratio; or in a case in which the maximum value of the spin echo intensities of the plural components to be weighted is higher than the minimum value of the spin echo intensities of the other plural components, the maximum value and the minimum value may be used for computing the contrast ratio.

(Image Generation Processing)

An example of image generation processing in which an MRI image is generated by applying a specific pulse train to the sample 1 will now be described. The image generation processing is executed by the controller 51, for example, in response to start manipulation from the operation unit 70 by a user. The sample 1 mounted on the mount stage 2 is set in the bore 3 before the start of the image generation processing.

Upon the start of the image generation processing, first, the controller 51 drives the static magnetic field coil 10 through a static magnetic field coil driver which is not illustrated, to form a uniform static magnetic field in the bore 3 (step S11). Before the image generation processing, a static magnetic field may be formed in the bore 3 in advance.

Subsequently, the controller 51 sets a $\pi$ pulse interval $2\tau$ in the case of applying the specific pulse train (step S12). First, the controller 51 accepts, from the operation unit 70, a manipulation of selecting a component intended to be weighted by a user. The component intended to be weighted, which is a component included in the sample 1, is a freely-selected component to be weighted in this case. The controller 51 sets the specific interval Ts corresponding to the component selected in this case as the $\pi$ pulse interval $2\tau$, with reference to the table data which is prepared in the storage 52 in advance, and in which the component to be weighted, and the specific interval Ts and specific period Ps are associated with each other. The controller 51 acquires the specific period Ps corresponding to the component selected in this case. For example, in a case in which the selected component is "urine" as illustrated in FIG. 6, the controller 51 acquires the specific interval Ts and the specific period Ps corresponding to "urine" with reference to the table data. The controller 51 drivingly controls the gradient magnetic field generator 20 and the pulse applicator 30 in such a manner as described below, for example, on the basis of pulse train data which is input through the operation unit 70 by a user in advance and stored in the storage 52.

Subsequently, the controller 51 applies, to the sample 1, RF pulses including the specific pulse train illustrated in FIG. 2 (step S13). Specifically, the specific interval Ts as the π pulse interval 2τ set in step S12 is read out, first, π/2 pulse is applied, and a π pulse is applied after a lapse of time τ (that is, Ts/2). Once the π pulse is applied, π pulses are consecutively applied at an interval of time 2τ (that is, the specific interval Ts)

Subsequently, the controller 51 detects the intensity of a spin echo, generated by applying each π pulse, through the RF coil 31 and the receiver 40 (step S14). For example, the spin echo intensity is read out through the RF coil 31 and the receiver 40 by the frequency encoding gradient magnetic field Gr applied at an interval of 2τ from the start of the application of the π/2 pulse.

Subsequently, the controller 51 collects a spin echo intensities in the specific period Ps acquired in step S12 from the spin echo intensities detected in step S14 (step S15), and allows the spin echo intensities to be stored in the storage 52.

Subsequently, the controller 51 generates an MRI image from the spin echo intensities in the specific period Ps, stored in step S15 (step S16), and allows the display 60 to display the generated MRI image. In the MRI image described in such a manner, a contrast capable of distinctly discriminating a component to be weighted and the other components from each other is generated between the component to be weighted and the other components.

For example, in a case in which the sample 1 is the mimic kidney, and "urine" is weighted (in a case in which the component selected in step S12 is "urine"), the controller 51 allows the spin echo intensities in the specific period Ps predetermined as a period suitable for observing "urine" to be stored in the storage 52 in step S15 by the image generation processing. In step S16, the image generator 51b of the controller 51 generates the MRI image according to the spin echo intensity in each coordinate space by subjecting the MR signals acquired in the specific period Ps to phase encoding under a gradient magnetic field and subjecting them to fast Fourier transform. In the spin echo intensities detected in the specific period Ps, the spin echo intensity derived from "urine" is higher than the spin echo intensities derived from "saline solution" and "gel", as illustrated in FIG. 6. As a result, the MRI image with a positive contrast in which "urine" is represented with a higher intensity than the intensities of the other components can be obtained. The MRI image with light and shade according to the spin echo intensity of each component in the specific period Ps illustrated in FIG. 6 (the MRI image with a high contrast in which the urine is more distinctly represented than the saline solution and the gel) can be obtained in such a manner. In other words, it is possible to obtain the MRI image for the mimic kidney, in which the ureter tissue is more distinctly represented than the kidney tissue and the vascular tissue. Likewise, it is also possible to obtain an MRI image with a positive or negative contrast in which "saline solution" or "gel" is weighted in the mimic kidney.

In a case in which the number of times of application of a π pulse is used instead of the specific period Ps, the controller 51 sets, as a π pulse interval 2τ, a specific interval Ts corresponding to the specific component selected in such a case, with reference to table data in which specific components, and specific intervals Ts and the specific numbers n of times are associated with each other, prepared in the storage 52 in advance, in step S12, and the controller 51 may acquire the specific number n of times corresponding to the specific component selected in such a case, apply a π pulse at least the specific number n of times in step S13, and, in step S15, collect the intensity of a spin echo generated by the n-th application of a π pulse acquired in step S12, n being the specific number n of times, allow the spin echo intensity to be stored in the storage 52, and perform the other items in a manner similar to that of the image generation processing described above.

In the image generation processing described above, the intensity of the spin echo generated by applying each π pulse of the specific pulse train is acquired in step S14. However, it is also acceptable to acquire only the intensity of a spin echo generated by applying a π pulse in the specific period Ps. In such a case, it is also acceptable that in step S13, the pulse controller 51a applies a phase encoding pulse only to a spin echo generated in the specific period Ps, and does not apply the phase encoding pulse to spin echoes generated before the specific period Ps and after a lapse of the specific period Ps.

(Focus Condition Determination Processing)

An example of focus condition determination processing in which focus conditions including a specific interval Ts and a specific period Ps or the specific number n of times are experientially determined will be described below. The focus condition determination processing is performed using the MRI apparatus 100 described above. The focus condition determination processing is executed by the controller 51, for example, according to start manipulation from the operation unit 70 by a user. Before the start of the focus condition determination processing, the first to p-th (p is a natural number of 2 or more) reference samples instead of the sample 1 are mounted on the mount stage 2, and set in the bore 3.

When the focus condition determination processing is started, first, the controller 51 drives the static magnetic field coil 10 through a static magnetic field coil driver which is not illustrated, to form a uniform static magnetic field in the bore 3 (step S21). Before the processing, a static magnetic field may be formed in the bore 3 in advance.

Subsequently, the controller 51 set a π pulse interval 2τ in the case of applying a specific pulse train at an initial value (step S22).

For example, in step S22, the controller 51 acquires a minimum pulse interval (for example, 5 microseconds) prepared in the storage 52 in advance, a maximum pulse interval (for example, 1 second), and a pulse interval increment width (for example, 0.1 microseconds), and sets the value of the minimum pulse interval at the value of the π pulse interval 2τ.

Subsequently, the controller 51 applies RF pulses including the specific pulse train illustrated in FIG. 2 to the first to p-th reference samples at least the predetermined number q of times (q is a natural number of 2 or more) (step S23). Specifically, first, a π/2 pulse is applied using the π pulse interval 2τ set in step S22, and a π pulse is applied after a lapse of time τ. After once the π pulse is applied, π pulses are consecutively applied at an interval of time 2τ.

Subsequently, the controller 51 detects the intensity of a spin echo generated from each of the first to p-th reference samples by applying the first to q-th π pulses, through the RF coil 31 and the receiver 40 (step S24). For example, the spin echo intensity is read through the RF coil 31 and the receiver 40.

Subsequently, the controller 51 determines whether or not to end loop processing of steps S23 and S24 (step S25). The process goes to step S26 when the loop processing is continued, while the process goes to step S27 when the loop processing is ended.

For example, in step S25, the loop processing is ended when a value obtained by increasing the value of the $\pi$ pulse interval $2\tau$ by the pulse interval increment width is more than the maximum pulse interval.

Subsequently, the $\pi$ pulse interval $2\tau$ is set at a subsequent candidate (step S26). Then, the process goes to step S23.

For example, in step S26, the $\pi$ pulse interval $2\tau$ is set at a value obtained by adding the pulse interval increment width to the current $\pi$ pulse interval $2\tau$.

Subsequently, with regard to each of one or more candidates for the specific period Ps or the specific number n of times, the controller 51 compares the spin echo intensities of the first to p-th reference samples acquired at pulse acquisition timing corresponding to the candidate, determines whether or not one reference sample of the first to p-th reference samples can be discriminated from the other reference samples on the basis of the spin echo intensities, and allows information indicating the one reference sample, the current candidate for the specific period Ps or the specific number n of times, and the current value of the $\pi$ pulse interval $2\tau$ to be stored as a table in the storage 52 when the discrimination is possible (step S27).

For example, in step S27, the controller 51 may acquire a list of the candidates for the specific period Ps prepared in the storage 52 in advance, and may compare the spin echo intensities of the first to p-th reference samples acquired in the candidate period, with regard to each of the candidates.

In step S27, the controller 51 may acquire a list for the candidates of the specific number n of times, prepared in the storage 52 in advance, and, with regard to each of the candidates, may compare the spin echo intensities of the first to p-th reference samples generated by applying the z-th $\pi$ pulse, z being the number of times of the candidate. For example, the candidate for the specific number n of times may be any of all natural numbers of 1 to q.

Whether or not one reference sample of the first to p-th reference samples can be discriminated from the other reference samples on the basis of spin echo intensities can be determined, for example, by the following procedure.

In the case of p≥3, in a case in which the spin echo intensities of the first to p-th reference samples are assigned with the first to p-th spin echo intensities in decreasing order of intensity, it is determined that the reference sample giving the first spin echo intensity can be discriminated from the other reference samples (a positive contrast is obtained) when a value obtained by dividing the first spin echo intensity by the second spin echo intensity is not less than a first predetermined value (for example, 2), and a value obtained by dividing the second spin echo intensity by the p-th spin echo intensity is less than a second predetermined value (for example, 1.2), and it is determined that the reference sample giving the q-th spin echo intensity can be discriminated from the other reference samples (a negative contrast is obtained) when a value obtained by dividing the q−1-th spin echo intensity by the q-th spin echo intensity is not less than the first predetermined value, and a value obtained by dividing the first spin echo intensity by the q−1-th spin echo intensity is less than the second predetermined value.

In the case of p=2, when a value obtained by dividing the spin echo intensity of the first reference sample by the spin echo intensity of the second reference sample is not less than a predetermined value (for example, 2), it is determined that the first reference sample can be discriminated from the second reference sample, then, the information of the first reference sample, the current candidate for the specific period Ps or the specific number n of times, and the current value of the $\pi$ pulse interval $2\tau$ are stored as positive contrast conditions in the table described above, and the information of the second reference sample, the current candidate for the specific period Ps or the specific number n of times, and the current value of the $\pi$ pulse interval $2\tau$ are stored as negative contrast conditions in the table described above. In addition, when a value obtained by dividing the spin echo intensity of the second reference sample by the spin echo intensity of the first reference sample is not less than a predetermined value (for example, 2), it is determined that the second reference sample can be discriminated from the first reference sample, then, the information of the second reference sample, the current candidate for the specific period Ps or the specific number n of times, and the current value of the $\pi$ pulse interval $2\tau$ are stored as positive contrast conditions in the table described above, and the information of the first reference sample, the current candidate for the specific period Ps or the specific number n of times, and the current value of the $\pi$ pulse interval $2\tau$ are stored as negative contrast conditions in the table described above.

Simultaneous measurement is performed for the first to p-th reference samples in the loop processing of steps S22 to S26 in the focus condition determination processing described above. However, it is also acceptable to perform individual measurement and to subject the data thereof in bulk to step S27.

In the focus condition determination processing described above, a method in which the pulse interval $2\tau$ is selected from one or more candidates is freely selected.

For example, it is also acceptable to set the maximum pulse interval instead of the minimum pulse interval at the initial value of the pulse interval $2\tau$ in step S22, to end the loop processing when a value obtained by subtracting the pulse interval increment width from the value of the $\pi$ pulse interval $2\tau$ is less than the minimum pulse interval in step S25, and to set the $\pi$ pulse interval $2\tau$ at a value obtained by subtracting the pulse interval increment width from the current $\pi$ pulse interval $2\tau$ in step S26.

For example, the controller 51 may acquire the list of the candidates for the specific interval Ts prepared in the storage 52 in advance, to set one of the candidates at the initial value of the $\pi$ pulse interval $2\tau$ in step S22, the controller 51 may end the loop processing in the case of using all the candidates of the list of the candidates for the specific interval Ts in step S25, and the controller 51 may set an unused candidate from the list of the candidates for the specific interval Ts at the $\pi$ pulse interval $2\tau$ in step S26.

As described above, when a spin echo intensity is normalized with a value at time zero in a fitted damped oscillation function in a case in which the sample 1 is measured by the MRI apparatus 100, the spin echo intensity is normalized in a similar manner in step S27, and then comparison thereof is performed.

A way of determining whether or not one reference sample of the first to p-th reference samples can be discriminated from the other reference samples on the basis of the spin echo intensities in step S27 is freely selected as long as the specific interval Ts and the specific interval Ps or the specific number n of times can be specified.

It is also acceptable that in step S27, with regard to each of one or more candidates for the specific period Ps or the specific number n of times, the controller compares the spin echo intensities of the first to p-th reference samples acquired at pulse acquisition timing corresponding to the candidate, determines whether or not a plurality of reference samples of the first to p-th reference samples can be discriminated from the other reference samples on the basis of the spin echo intensities, and allows information indicating the plurality of reference samples, the current candidate for the specific period Ps or the specific number n of times, and the current value of the π pulse interval 2τ to be stored as a table in the storage 52 when the discrimination is possible. In such a case, for example, it is possible to determine whether or not the plurality of reference samples of the first to p-th reference samples can be discriminated from the other reference samples on the basis of the spin echo intensities, by ranking the spin echo intensities of the first to p-th reference samples in decreasing order of intensity, grouping spin echo intensities into the first to r-th (r is a natural number of 2 or more) groups which are in decreasing order of spin echo intensity and each of which includes similar spin echo intensities, and determining contrast ratios between the first to fourth groups. For example, such grouping can be performed so that a value obtained by dividing the maximum value of spin echo intensities included in a certain group by the minimum value thereof is less than a predetermined threshold value (for example, 1.2). The comparison of the contrast ratios between the groups may be performed based on the average value of spin echo intensities in each group, or may be performed based on the minimum value of the x-th (x is a natural number) group and the maximum value of the y-th (y is a natural number that is more than x) group.

In step S27, the focus conditions are comprehensively examined with regard to all the reference samples. However, when a component intended to be weighted is determined in advance, it may be determined whether or not the spin echo intensity of the reference sample corresponding to the component can be discriminated from the other reference samples on the basis of spin echo intensities. In step S27, the focus conditions are determined for both the negative contrast and the positive contrast. However, it is also acceptable to determine focus conditions for only one contrast. For example, in a case in which the first reference sample of the first and second reference samples is a component intended to be weighted, and only focus conditions under which the first reference sample exhibits a positive contrast with respect to the second reference sample may be determined, in step S27, it is determined that the first reference sample can be discriminated from the second reference sample when a value obtained by dividing the spin echo intensity of the first reference sample by the spin echo intensity of the second reference sample is not less than a predetermined value (for example, 2), and then, the information of the first reference sample, the current candidate for the specific period Ps or the specific number n of times, and the current value of the π pulse interval 2τ may be stored as positive contrast conditions in the table described above.

(Effects of MRI Apparatus)

Although only MRI images without clear created contrast have been able to be obtained by the conventional techniques, an MRI image in which a desired site is weighted and which has a clear positive or negative contrast can be obtained by the MRI apparatus 100 using the specific pulse train described above. The technique of generating an image by the MRI apparatus 100 can address social and economical requirements because realization of the technique can be expected by introducing a program PG1 for executing image generation processing into an existing MRI apparatus. The technique of generating an image by the MRI apparatus 100 also has an excellent feature in that the sample 1 as a subject can be subjected to nondestructive inspection. In addition, the MRI apparatus 100 is excellent in view of being capable of focusing on a desired site in a tissue to selectively create a clear contrast without using a contrast medium.

A case in which the sample 1 is the kidney of a test subject is taken as an example. Currently, it is a reality that one of eight adults in the country suffers from chronic kidney disease, and about 320,000 people undergo artificial dialysis. However, renal biopsy widely used as a method of diagnosis of renal disease has imposed great loads on patients due to the invasiveness of the renal biopsy. In this regard, the technique of generating an image by the MRI apparatus 100, described above, enables high-precision examination while reducing loads on patients.

The present disclosure is not limited to the embodiment described above, and the drawings. Modifications (including deletion of a component) can be made to the present disclosure, as appropriate, as long as the gist of the present disclosure is not changed.

The sample 1 to be imaged is freely selected, and, for example, may be an organ other than the kidney, may be a site other than the organs of a human body or an animal, or may be a plant. The sample 1 may be the whole body of a human or an animal. Further, the sample 1 may be a body fluid (blood, serum, lymph fluid, cerebrospinal fluid, sweat, urine, or the like), a cultured cell, a microorganism, a mimic organ or mimic body fluid mimicking a living body, or any liquid or solid. Selection of the sample 1 and a manner of classifying components included in the sample 1 are freely performed as long as the specific interval Ts and specific period Ps of a π pulse, in which a difference between the signal intensity of the spin echo of a specific component of the plural components included in the sample 1 and the signal intensities of the spin echoes of the other components is noticeable, can be experientially determined.

The configuration of the MRI apparatus 100 is also freely selected as long as a static magnetic field, a gradient magnetic field, and an RF magnetic field can be applied to the sample 1. Various configurations can be adopted as the configuration of the MRI apparatus 100.

In the image generation processing described above, not only the specific interval Ts but also the specific period Ps is experientially determined. However, it is also acceptable to experientially determine only the specific interval Ts which is an interval of application of a π pulse. In such a case, for example, the controller 51 may detect the spin echo intensity of each component of the sample 1 on a time-series basis, and may generate an MRI image on the basis of a spin echo intensity in a case in which a ratio between the spin echo intensity of a specific component and the spin echo intensity of another component (a value obtained by dividing the higher intensity by the lower intensity) is not less than a threshold value determined in advance.

Under present circumstances, it has not been theoretically clear why a spin echo intensity characteristic varies according to a component included in the sample 1 by changing an interval of application of a π pulse in a specific pulse train. In a case in which a theory on which the characteristic is elucidated is constructed in the future, a specific interval Ts and a specific period Ps may be derived based on the theory.

A technique of performing frequency analysis of an MR signal is not limited to two-dimensional Fourier transform, and another known frequency analysis method may be used as the technique. In the case of performing Fourier transform, fast Fourier transform (FFT) is preferably executed.

Rearrangement, change, or addition of processes included in the image generation processing is optional as long as the specific pulse train described above can be applied to the sample 1, and a spin echo generated by applying each π pulse can be detected.

The programs PG1 and PG2 for executing each process described above are stored in the storage 52 in advance. However, the programs may be distributed and provided by a removable non-transitory recording medium. The programs PG1 and PG2 may be downloaded from another instrument connected to the MRI apparatus 100. The MRI apparatus 100 may execute each process according to the programs PG1 and PG2 by exchanging various data with another instrument through an electrical communication network or the like.

The MRI apparatus 100 in which a pulse echo signal obtained by application of a specific pulse train is used for forming an MRI image is described above. However, an NMR apparatus in which a specific component and another component are discriminated and detected using a pulse echo signal obtained by application of a specific pulse train can also be configured. Examples of such NMR apparatuses include common NMR apparatuses which are apparatuses configured so that the above-described specific pulse train can be applied to a sample, for example, an apparatus illustrated in FIG. 5, and the like. Even in the case of such an apparatus, when with regard to each of plural components which are options to be detected, a specific interval Ts and a specific period Ps or the specific number n of times in which the component can be discriminated based on the spin echo intensities of the other components are experientially determined in advance, whether or not a certain sample is a specific component can be estimated based on a spin echo intensity acquired at timing corresponding to the specific period Ps or the specific number n of times by applying a specific pulse train to the sample at the specific interval Ts corresponding to the specific component.

In the above description, explanations of the known technological items have been omitted to facilitate understanding of the present disclosure, as appropriate.

EXAMPLES

Example 1

Using an NMR apparatus that detects $^{23}$Na, one π/2 pulse (excitation pulse) and plural π pulses (reverse pulses) were applied to a sample put in a test tube in a static magnetic field according to the APCP pulse train illustrated in FIG. 2 at various pulse intervals τ, and plural spin echo signals obtained from the sample were measured.

Figure 5:
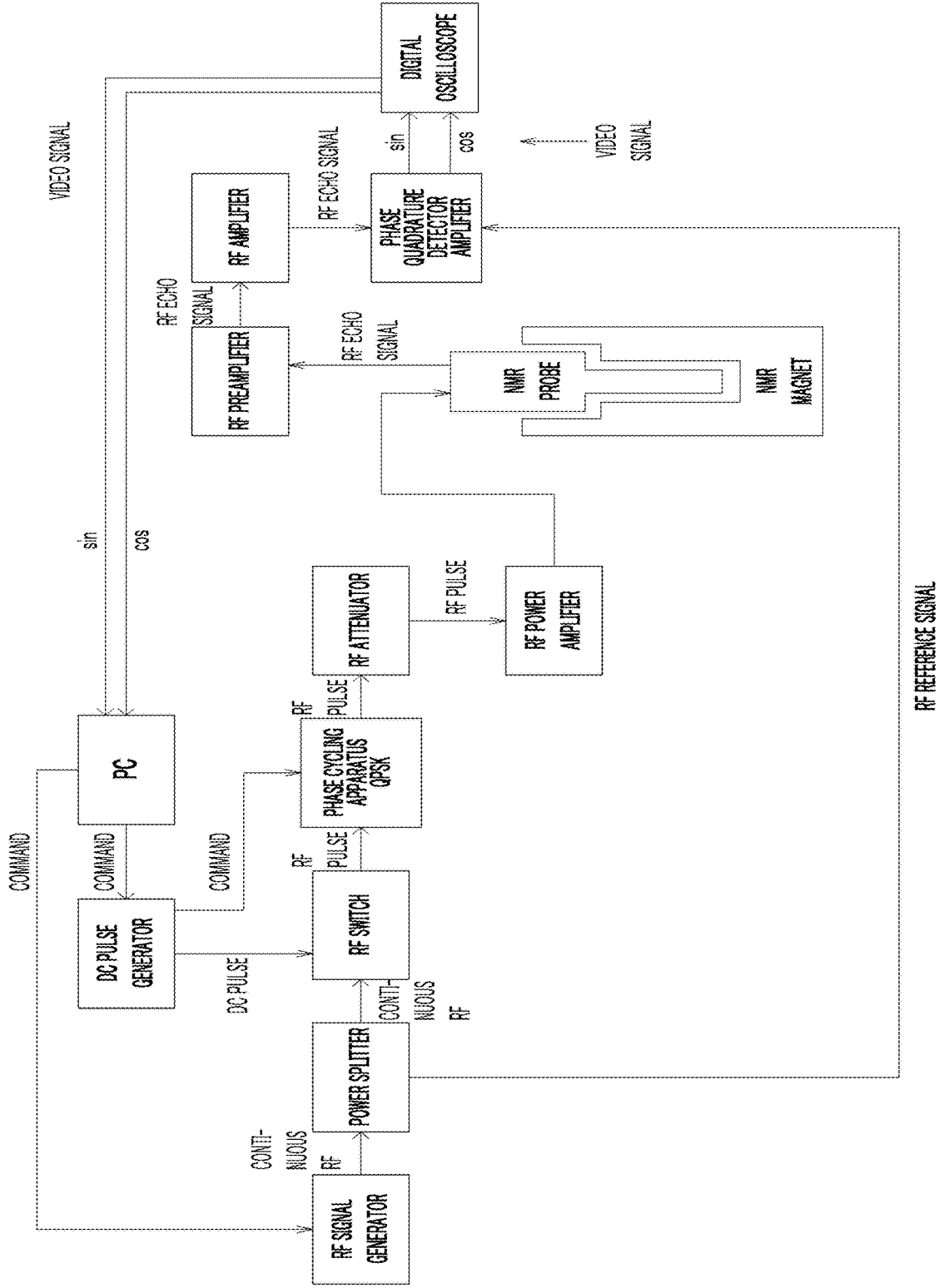
FIG. 5 is a block diagram illustrating the configuration of an NMR apparatus used in Examples.

The NMR apparatus described above can be configured as illustrated in the block diagram of FIG. 5, and primarily includes an NMR magnet and a probe (Oxford room-temperature bore high-resolution NMR superconducting magnet, Oxford 300/89, made in U.K.), an RF signal generator (HP8656B, made in U.S.A.), a DC pulse generator (DC Pulse Programmer, THAMWAY Corp., N210-10265, made in Japan), an RF attenuator (a programmable attenuator, TAMAGAWA ELECTRONICS CO., LTD., TPA-410, made in Japan), an RF power amplifier (DotyDSI1000B, made in U.S.A.), an RF preamplifier (Doty2LSeries, made in U.S.A.), and the like.

As such samples, three kinds of samples, which were saline solution, urine, and gel, were used. A saturated saline solution was used as the saline solution. The urine, which was of human origin and included 4 to 14 g/dL of Na, was used. The gel was produced by adding a saturated amount of gelatin powder ("Cook Gelatin", MORINAGA & CO., LTD.) and 2 to 3% by weight of salt to urban water, and solidifying the resultant. About 5 mL of each sample was used for measurement.

Figure 7:
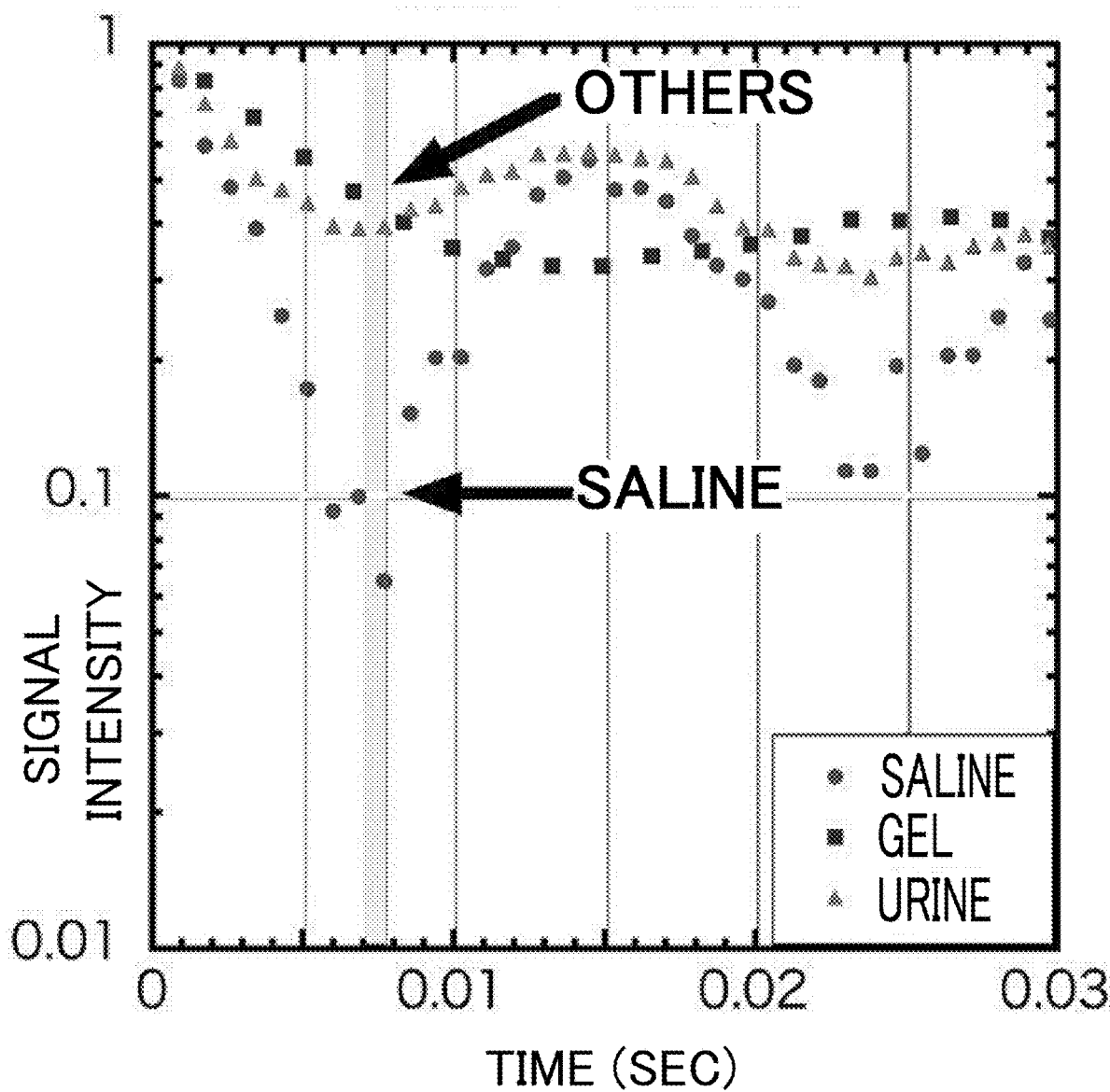
FIG. 7 is a diagram of another graph indicating spin echo intensity in the case of applying a specific pulse train to saline solution, gel, and urine with $^{23}$Na as an atom to be measured.
Figure 8:
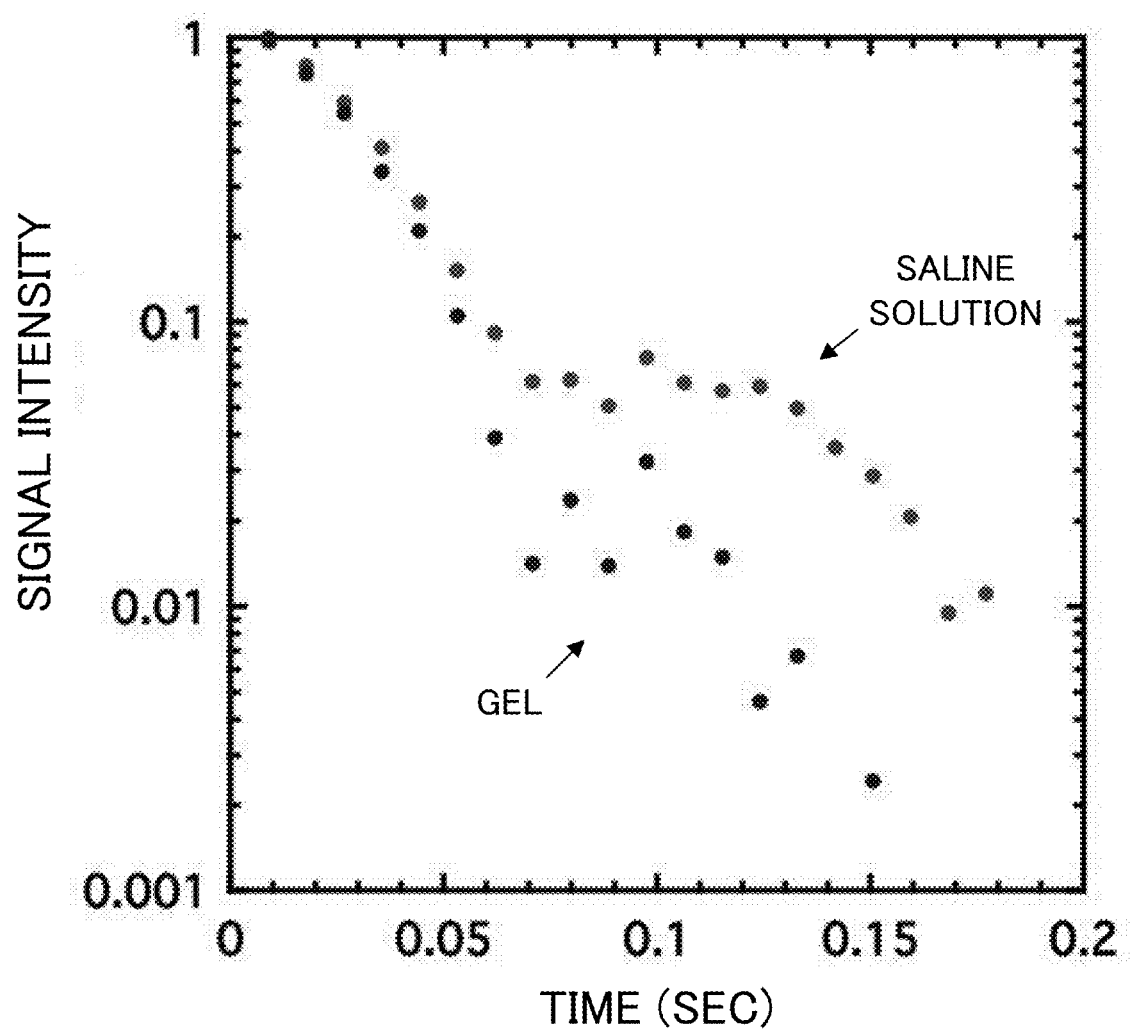
FIG. 8 is a diagram of a graph indicating spin echo intensity in the case of applying a specific pulse train to saline solution and gel with $^{23}$Na as an atom to be measured.

Some of the results of measurement performed at the various pulse intervals τ are illustrated in FIGS. 6 to 8. When the APCP pulse train illustrated in FIG. 2 is applied to saline solution, urine, and gel in a case in which the pulse width of π/2 pulse is set at 16 microseconds, the pulse width of a π pulse is set at 24 microseconds, and a pulse interval 4τ is set at 0.86 milliseconds, the signal intensities of spin echo signals generated from the saline solution, the urine, and the gel by the application of each π pulse (only those generated by the application of π pulses (180×) illustrated in an upward direction in FIG. 2) are plotted with respect to time from irradiation with the π/2 pulse to acquisition of the spin echo signals in FIG. 6. In the figure, the signal intensity of the spin echo signal of each sample is indicated based on a value normalized with respect to an extrapolation value at time zero. Accordingly, the signal intensities at time zero are 1 with regard to all the samples. Likewise, FIG. 7 illustrates results in a case in which the pulse width of π/2 pulse is 16 microseconds, the pulse width of a π pulse is set at 24 microseconds, and a pulse interval 4τ is set at 1.67 milliseconds for gel and at 0.835 milliseconds for saline solution and urine, while FIG. 8 illustrates results in a case in which only saturated saline solution and gel are used, the pulse width of π/2 pulse is set at 16 microseconds, the pulse width of a π pulse is set at 26 microseconds, and a pulse interval τ is set at 2.2 milliseconds.

Example 2

Using the NMR apparatus described in Example 1, with $^1$H as an atom to be measured instead of $^{23}$Na, one π/2 pulse (excitation pulse) and plural π pulses (reverse pulses) were applied to a sample in a static magnetic field according to the APCP pulse train illustrated in FIG. 2 at various pulse intervals τ, and plural spin echo signals obtained from the sample were measured. The pulse width of π/2 pulse was set at 20 microseconds, and the pulse width of a π pulse was set at 50 microseconds. A pulse interval τ was set at 1, 1.5, 2, 3, 4, or 5 milliseconds.

A gel produced by adding a saturated amount of gelatin powder and 2% by weight of salt to urban water, and solidifying the resultant was used as the sample. Only about 5 mL of the gel was put in a test tube, and the test tube was placed in the static magnetic field of the NMR apparatus, and used for measurement.

Figure 9:
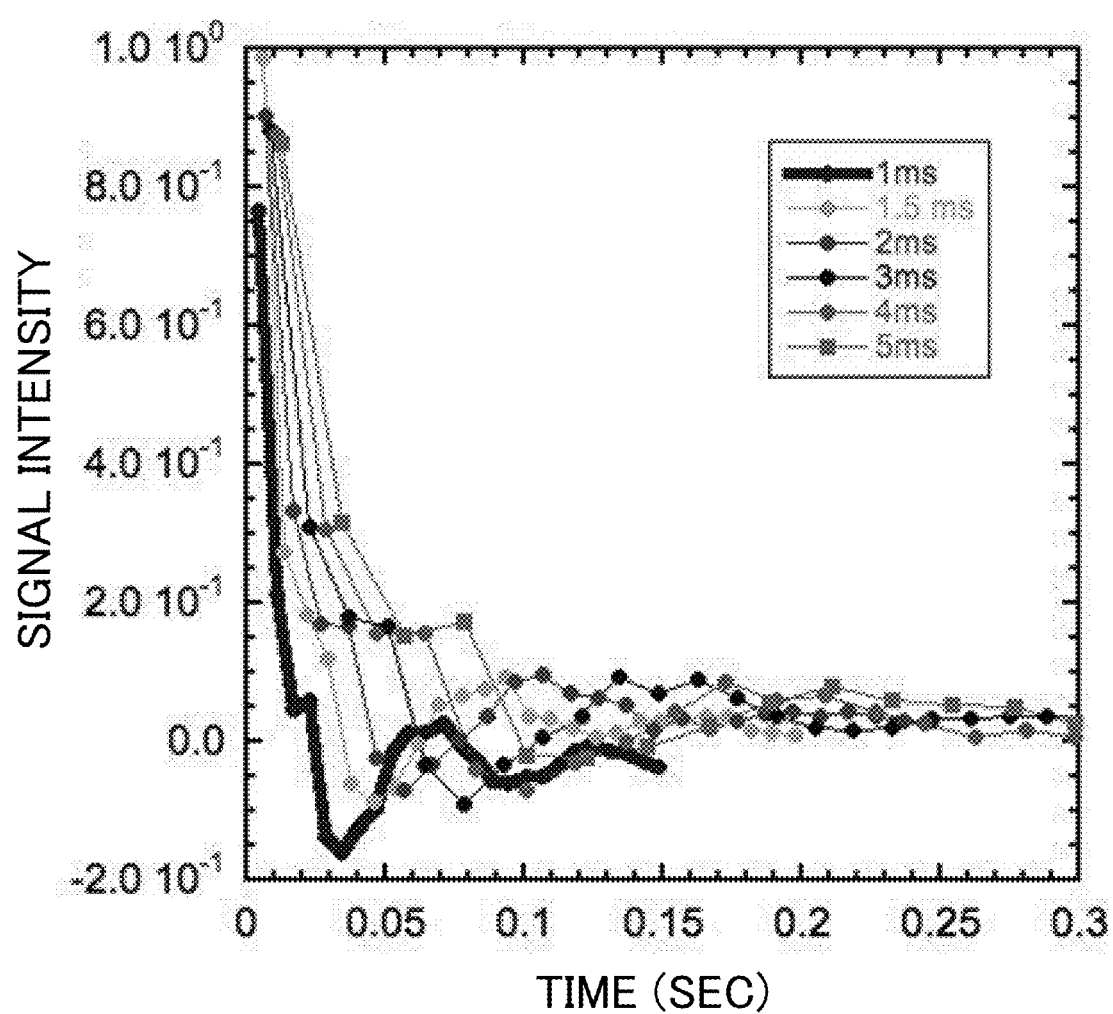
FIG. 9 is a diagram of a graph indicating spin echo intensity in the case of applying a specific pulse train to gel with $^1$H as an atom to be measured.

The measurement results are illustrated in FIG. 9. When the APCP pulse train illustrated in FIG. 2 is applied to the gel at each of the pulse intervals τ described above, the signal intensities of spin echo signals generated from the gel by the application of each π pulse are plotted with respect to time from irradiation with the π/2 pulse to acquisition of the spin echo signals, in FIG. 9. The standardization of the signal intensities is similar to that in Example 1.

Comparative Example 1

Figure 10:
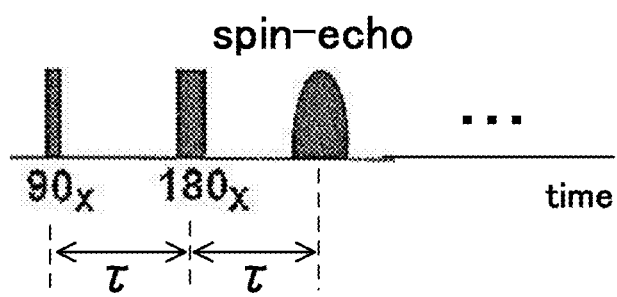
FIG. 10 is a diagram illustrating a pulse train according to a conventional example.

The spin echo signals obtained from saline solution, urine, and gel were measured by a Hahn echo method using the NMR apparatus described in Example 1 with $^{23}$Na as an atom to be measured. In the Hahn echo method, as illustrated in FIG. 10, a π pulse (reverse pulse) is applied only once after time τ after application of π/2 pulse (excitation pulse), the signal intensity (echo intensity) of a spin echo signal obtained after time τ is then obtained as a function of a pulse interval 2τ, and therefore, corresponding echo intensities are sequentially acquired while experimentally chronologically changing τ. The pulse width of the π/2 pulse was set at 16 microseconds, and the pulse width of a pulse was set at 24 microseconds.

The results of the measurement by the Hahn echo method are illustrated in FIG. 11. The signal intensities of spin echo signals generated from saline solution, urine, or gel by the application of the π pulse are plotted with respect to time from irradiation with the π/2 pulse to acquisition of the spin echo signals, in FIG. 11.

(Summarization)

First, the results of FIGS. 6 to 8, described in Example 1, show that application of the specific pulse train illustrated in FIG. 2 to saline solution, gel, and urine allows the signal intensities of plural spin echoes generated by applying each π pulse to exhibit damped oscillation. Comparison of FIGS. 6 to 8 shows that the damped oscillation pattern of each sample exhibits a pattern varying depending on (a) the kind of the component of the sample, and (b) a pulse application interval in a specific pulse train. In particular, it is found that (c) the damped oscillation pattern of a different sample does not necessarily fluctuate in a linking manner but exhibits a different fluctuation according to the kind of each sample in the case of changing the pulse application interval in the specific pulse train.

If the characteristics of the damping oscillation resulting from a specific pulse train are used, such a combination of the damped oscillation patterns of the samples that different samples can be discriminated based on spin echo intensity is obtained by variously changing a pulse application interval in the specific pulse train.

In the case of taking a camera as an example, the characteristics correspond to obtainment of a movable focus. The conventional spin echo method illustrated in FIG. 11 corresponds to imaging with a fixed focus in which it is impossible to definitely obtain the contrast of a specific component with respect to the other components in the case of observing a specific component because a difference in the signal intensity of a spin echo between components to be examined is not noticeable in both echo times TE1 and TE2.

However, since utilization of the characteristics described above enables change of spin echo characteristics between components included in an object to be examined by varying an interval at which a π pulse is applied, control of a pulse application interval in a variable manner according to a specific component included in a sample corresponds to imaging with a movable focus in which an optional object can be put into the focus. Accordingly, in the case of utilizing the characteristics, an MRI image in which a specific component is put into focus is generated by experientially determining, in advance, a specific interval at which a π pulse is applied, and spin echo acquisition timing, in which a difference between the signal intensity of the spin echo of the specific component and the signal intensity of the spin echo of another component of plural components included in an object to be examined is noticeable, and by controlling an interval, at which a pulse in a specific pulse train is applied, to the specific application interval described above when the specific pulse train is applied to the object to be examined, to perform control corresponding to movable control of a focus in a camera.

As illustrated in Example 2, it is found that a damped oscillation pattern with a spin echo intensity is obtained by applying a specific pulse train even in the case of regarding not only $^{23}$Na but also $^{1}$H as a target for measurement. Accordingly, it is considered that a focus control technology based on the specific pulse train described above can be applied not only to $^{23}$Na but also to various other atoms.

The program described in the present embodiment can be recorded in a non-transitory computer-readable information recording medium, distributed, and sold. The program can be distributed and sold through a transitory transmission medium such as a computer communication network.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the priority of Japanese Patent Application No. 2018-036934, filed on Mar. 1, 2018, the entire disclosure of which is incorporated by reference herein.

REFERENCE SIGNS LIST

100 MRI apparatus
1 Sample
2 Mount stage
3 Bore
10 Static magnetic field coil
20 Gradient magnetic field generator
21 Gradient magnetic field coil
22 Gradient magnetic field coil driver
30 Pulse applicator
31 RF coil
32 RF coil driver
40 Receiver
50 Control apparatus
51 Controller
51a Pulse controller
51b Image generator
52 Storage
PG1, PG2 Program
60 Display
70 Operation unit

The invention claimed is:

1. A nuclear magnetic resonance apparatus comprising:
a static magnetic field former that forms a static magnetic field;
an object holder that holds an object in the static magnetic field;
a pulse applicator that applies a π/2 pulse having a Larmor frequency of an atom to be measured to the object in the static magnetic field and then applies a π pulse having the Larmor frequency to the object at least a predetermined number of times (the predetermined number being two or more) at an interval of a predetermined period, the π pulse being applied for a first time at a time point at which half the predetermined period has elapsed after applying the π/2 pulse, and the π pulses being applied as a pulse train comprising a plurality of π pulses with alternating polarities; and a detector that detects a signal intensity of a spin echo signal generated from the object as a result of a last instance of the predetermined number of times of application of the π pulse, wherein in a case in which: the π/2 pulse is applied to a first component in the static magnetic field and then the π pulse is applied to the first component at least the predetermined number of times at an interval of the predetermined period, the π pulse being applied for a first time at a time point at which half the predetermined period has elapsed after applying the π/2 pulse; a signal intensity of a spin echo signal generated from the first component as a result of a last instance of the predetermined number of times of the application of the π pulse is regarded as a first signal intensity; the π/2 pulse is applied to a second component in the static magnetic field and then the π pulse is applied to the second component at least the predetermined number of times at an interval of the predetermined period, the π pulse being applied for a first time at a time point at which half the predetermined period has elapsed after applying the π/2 pulse; and a signal intensity of a spin echo signal generated from the second component as a result of a last instance of the predetermined number of times of the application of the π pulse is regarded as a second signal intensity, the predetermined period and the predetermined number of times are set so that and the first signal intensity and the second signal intensity are made to differ from each other to an extent that: the first component and the second component can be discriminated from each other;

and a difference between the first component and the second component is detectable.

2. The nuclear magnetic resonance apparatus according to claim 1, wherein in the pulse applicator, it is possible to change the predetermined period in a range of 5 μs or more and 1 μs or less.

3. A magnetic resonance imaging apparatus comprising: the nuclear magnetic resonance apparatus according to claim 1; and an image generator that generates an image based on the signal intensity detected by the detector.

4. The magnetic resonance imaging apparatus according to claim 3, wherein the π pulses are applied as alternating polarity Carr Purcell.

5. The nuclear magnetic resonance apparatus according to claim 1, wherein the π pulses are applied as alternating polarity Carr Purcell.

6. A nuclear magnetic resonance method comprising:

a step of applying a π/2 pulse having a Larmor frequency of an atom to be measured to an object in a static magnetic field, and then applying a π pulse having the Larmor frequency to the object at least a predetermined number of times (the predetermined number being two or more) at an interval of a predetermined period, the π pulse being applied for a first time at a time point at which half the predetermined period has elapsed after applying the π/2 pulse and the π pulses being applied as a pulse train comprising a plurality of π pulses with alternating polarities; and a step of detecting a signal intensity of a spin echo signal generated from the object as a result of a last instance of the predetermined number of times of application of the π pulse, wherein in a case in which: the π/2 pulse is applied to a first component in the static magnetic field and then the π pulse is applied to the first component at least the predetermined number of times at an interval of the predetermined period, the π pulse being applied for a first time at a time point at which half the predetermined period has elapsed after applying the π/2 pulse; a signal intensity of a spin echo signal generated from the first component as a result of a last instance of the predetermined number of times of the application of the π pulse is regarded as a first signal intensity; the π/2 pulse is applied to a second component in the static magnetic field and then the pulse is applied to the second component at least the predetermined number of times at an interval of the predetermined period, the π pulse being applied for a first time at a time point at which half the predetermined period has elapsed after applying the π/2 pulse; and a signal intensity of a spin echo signal generated from the second component as a result of a last instance of the predetermined number of times of the application of the π pulse is regarded as a second signal intensity, the predetermined period and the predetermined number of times are set so that and the first signal intensity and the second signal intensity are made to differ from each other to an extent that: the first component and the second component can be discriminated from each other; and a difference between the first component and the second component is detectable.

7. A magnetic resonance imaging method comprising:

a step of generating an image of the object based on the signal intensity detected by the nuclear magnetic resonance method according to claim 6.

8. The magnetic resonance imaging method according to claim 7, wherein then pulses are applied as alternating polarity Carr Purcell.

9. The nuclear magnetic resonance method according to claim 6, wherein the π pulses are applied as alternating polarity Carr Purcell.

10. A non-transitory computer-readable information recording medium storing a program allowing a computer to function as:

pulse application means that allows a pulse applicator to apply a π/2 pulse having a Larmor frequency of an atom to be measured to an object in a static magnetic field, and then apply a π pulse having the Larmor frequency to the object at least a predetermined number of times (the predetermined number being two or more) at an interval of a predetermined period, the π pulse being applied for a first time at a time point at which half the predetermined period has elapsed after applying the π/2 pulse, and the π pulses being applied as a pulse train comprising a plurality of π pulses with alternating polarities; and detection means that allows a detector to detect a signal intensity of a spin echo signal generated from the object as a result of a last instance of the predetermined number of times of application of the π pulse, wherein in a case in which: the π/2 pulse is applied to a first component in the static magnetic field and then the π pulse is applied to the first component at least the predetermined number of times at an interval of the predetermined period, the π pulse being applied for a first time at a time point at which half the predetermined period has elapsed after applying the π/2 pulse; a signal intensity of a spin echo signal generated from the first component as a result of a last instance of the predetermined number of times of the application of the π pulse is regarded as a first signal intensity; the π/2 pulse is applied to a second component in the static magnetic field and then the pulse is applied to the second component at least the predetermined number of times at an interval of the predetermined period, the π pulse being applied for a first time at a time point at which half the predetermined period has elapsed after applying the π/2 pulse; and a signal intensity of a spin echo signal generated from the second component as a result of a last instance of the predetermined number of times of the application of the π pulse is regarded as a second signal intensity, the predetermined period and the predetermined number of times are set so that and the first signal intensity and the second signal intensity are made to differ from each other to an extent that: the first component and the second component can be discriminated from each other; and a difference between the first component and the second component is detectable.

11. The non-transitory computer-readable information recording medium according to claim 10, allowing the computer to further function as image generation means that generates an image of the object based on the signal intensity.

12. The non-transitory computer-readable information recording medium according to claim 10, wherein the π pulses are applied as alternating polarity Carr Purcell.

13. A method for determining a measurement condition comprising a predetermined period and/or a predetermined number of times in a nuclear magnetic resonance method comprising: applying a π/2 pulse having a Larmor frequency of an atom to be measured to an object in a static magnetic field, and then applying a π pulse having the Larmor frequency to the object at least the predetermined number of times (the predetermined number being two or more) at an interval of the predetermined period, the π pulse being applied for a first time at a time point at which half the predetermined period has elapsed after applying the π/2 pulse, and the π pulses being applied as a pulse train comprising a plurality of π pulses with alternating polarities; and detecting a signal intensity of a spin echo signal generated from the object as a result of a last instance of the predetermined number of times of application of the π pulse, wherein, in a case in which: one or more candidate periods are candidates for the predetermined period; and one or more candidate numbers of times are candidates for the predetermined number of times, the method for determining a measurement condition comprises:

a first pulse application step of, for each of the candidate periods, applying the π/2 pulse to a first reference object in the static magnetic field and applying the π pulse to the first reference object at least a greatest number of the candidate numbers of times at an interval of the candidate period, the π pulse being applied for a first time at a time point at which half the candidate period has elapsed after applying the π/2 pulse;

a first signal detection step of, for each of candidate numbers of times, detecting, as a first signal intensity, a signal intensity of a spin echo signal generated from the first reference object by applying the π pulse as a result of a last instance of the candidate number of times in the first pulse application step;

a second pulse application step of, for each of the candidate periods, applying the π/2 pulse to a second reference object in the static magnetic field and then consecutively applying the it pulse to the second reference object at least the greatest number of the candidate numbers of times at an interval of the candidate period, the π pulse being applied for a first time at a time point at which half the candidate period has elapsed after applying the π/2 pulse;

a second signal detection step of, for each of the candidate numbers of times, detecting, as a second signal intensity, a signal intensity of a spin echo signal generated from the second reference object by applying the π pulse as a result of a last instance of the candidate number of times in the second pulse application step; and a condition determination step of, for each of the candidate periods and for each of the candidate numbers of times, determining the candidate period as one of the predetermined periods and/or determining the candidate number of times as one of the predetermined numbers of times in a case in which the first signal intensity and the second signal intensity differ from each other to an extent that: the first reference object and the second reference object can be discriminated from each other; and a difference between the first reference object and the second reference object is detectable, with regard to the first signal intensity corresponding to the application of the π pulse as the result of the last instance of the candidate number of times in the first pulse application step performed at an interval of the candidate period and the second signal intensity corresponding to the application of the π pulse as the result of the last instance of the candidate number of times in the second pulse application step performed at an interval of the candidate period.

14. The method for determining a measurement condition according to claim 13, wherein the π pulses are applied as alternating polarity Carr Purcell.

15. A non-transitory computer-readable information recording medium storing a program that determines a measurement condition comprising a predetermined period and/or a predetermined number of times in a nuclear magnetic resonance method comprising: allowing a pulse applicator to apply a π/2 pulse having a Larmor frequency of an atom to be measured to an object in a static magnetic field and then apply a π pulse having the Larmor frequency to the object at least the predetermined number of times (the predetermined number being two or more) at an interval of the predetermined period, the π pulse being applied for a first time at a time point at which half the predetermined period has elapsed after applying the π/2 pulse, and the π pulses being applied as a pulse train comprising a plurality of π pulses with alternating polarities; and allowing a detector to detect a signal intensity of a spin echo signal generated from the object as a result of a last instance of the predetermined number of times of application of the π pulse, wherein, in a case in which: one or more candidate periods are candidates for the predetermined period; and one or more candidate numbers of times are candidates for the predetermined number of times, the program allows a computer to function as:

first pulse application means that allows the pulse applicator to, for each of the candidate periods, apply the π/2 pulse to a first reference object in the static magnetic field and then apply the π pulse to the first reference object at least a greatest number of the candidate numbers of times at an interval of the candidate period, the π pulse being applied for a first time at a time point at which half the candidate period has elapsed after applying the π/2 pulse;

first signal detection means that allows the detector to, for each of candidate numbers of times, detect, as a first signal intensity, a signal intensity of a spin echo signal generated from the first reference object by applying the π pulse as a result of a last instance of the candidate number of times in the first pulse application means;

second pulse application means that allows the pulse applicator to, for each of the candidate periods, apply the π/2 pulse to a second reference object in the static magnetic field at an interval of the candidate period and then apply the π pulse to the second reference object at least the greatest number of the candidate numbers of times at an interval of the candidate period, the π pulse being applied for a first time at a time point at which half the candidate period has elapsed after applying the π/2 pulse;

second signal detection means that allows the detector to, for each of the candidate numbers of times, detect, as a second signal intensity, a signal intensity of a spin echo signal generated from the second reference object by applying the π pulse as a result of a last instance of the candidate number of times in the second pulse application means; and condition determination means that, for each of the candidate periods and for each of the candidate numbers of times, determines the candidate period as one of the predetermined periods and/or determines the candidate number of times as one of the predetermined numbers of times in a case in which the first signal intensity and the second signal intensity differ from each other to an extent that: the first reference object and the second reference object can be discriminated from each other; and a difference between the first reference object and the second reference object is detectable, with regard to the first signal intensity corresponding to the application of the π pulse as the result of the last instance of the candidate number of times in the first pulse application means performed at an interval of the candidate period and the second signal intensity corresponding to the application of the π pulse as the result of the last instance of the candidate number of times in the second pulse application means performed at an interval of the candidate period.

16. The non-transitory computer-readable information recording medium according to claim 15, wherein the π pulses are applied as alternating polarity Carr Purcell.

* * * * *